(12) United States Patent
Lozano

(10) Patent No.: US 8,315,703 B2
(45) Date of Patent: Nov. 20, 2012

(54) METHODS FOR TARGETING DEEP BRAIN SITES TO TREAT MOOD AND/OR ANXIETY DISORDERS

(75) Inventor: Andres M. Lozano, Toronto (CA)

(73) Assignee: Advanced Neuromodulation Systems, Inc., Plano, TX (US)

( * ) Notice: Subject to any disclaimer, the term of this patent is extended or adjusted under 35 U.S.C. 154(b) by 666 days.

(21) Appl. No.: 12/433,335

(22) Filed: Apr. 30, 2009

(65) Prior Publication Data
US 2010/0057159 A1  Mar. 4, 2010

Related U.S. Application Data

(60) Provisional application No. 61/049,092, filed on Apr. 30, 2008.

(51) Int. Cl.
*A61N 1/36* (2006.01)
(52) U.S. Cl. .......................................................... 607/45
(58) Field of Classification Search .................... 607/45
See application file for complete search history.

(56) References Cited

U.S. PATENT DOCUMENTS

| | | | |
|---|---|---|---|
| 4,883,057 A | 11/1989 | Broderick |
| 5,540,734 A | 7/1996 | Zabara |
| 5,611,350 A | 3/1997 | John |
| 5,792,186 A | 8/1998 | Rise |
| 5,921,245 A | 7/1999 | O'Donnell, Jr. |
| 5,938,688 A | 8/1999 | Schiff |
| 5,975,085 A | 11/1999 | Rise |
| 6,016,449 A | 1/2000 | Fischell et al. |
| 6,128,537 A | 10/2000 | Rise |
| 6,132,361 A | 10/2000 | Epstein et al. |
| 6,161,045 A | 12/2000 | Fischell et al. |
| 6,176,242 B1 | 1/2001 | Rise |
| 6,216,030 B1 | 4/2001 | Howard et al. |
| 6,230,049 B1 | 5/2001 | Fischell et al. |
| 6,263,237 B1 | 7/2001 | Rise |
| 6,353,754 B1 | 3/2002 | Fischell et al. |
| 6,366,813 B1 | 4/2002 | DiLorenzo |
| 6,418,344 B1 | 7/2002 | Rezai |
| 6,425,852 B1 | 7/2002 | Epstein et al. |
| 6,463,328 B1 | 10/2002 | John |
| 6,473,639 B1 | 10/2002 | Fischell et al. |
| 6,591,138 B1 | 7/2003 | Fischell |

(Continued)

FOREIGN PATENT DOCUMENTS
WO   WO 01-97906   12/2001
(Continued)

OTHER PUBLICATIONS

Wingeier et al. Intra-operative STN DBS attenuates the prominent beta rhythm in the STN in Parkinson's disease. Experimental Neurology; (2006) 197:244-251.*

(Continued)

*Primary Examiner* — Carl H Layno
*Assistant Examiner* — Jeremiah Kimball
(74) *Attorney, Agent, or Firm* — Christopher S. L. Crawford; Craig Hoersten

(57) ABSTRACT

The present invention relates to a method of identifying a target such as within the subgenual area by measuring neuronal activity in response to a stimulus. Once the target is identified, it can be stimulated to treat a neurological disorder, such as a mood disorder or an anxiety disorder.

9 Claims, 16 Drawing Sheets

U.S. PATENT DOCUMENTS

| | | | |
|---|---|---|---|
| 6,597,954 B1 | 7/2003 | Pless et al. | |
| 6,609,030 B1 | 8/2003 | Rezai et al. | |
| 6,609,031 B1 | 8/2003 | Law et al. | |
| 6,708,064 B2 | 3/2004 | Rezai | |
| 6,735,475 B1 | 5/2004 | Whitehurst et al. | |
| 6,782,292 B2 | 8/2004 | Whitehurst | |
| 6,819,956 B2 | 11/2004 | DiLorenzo | |
| 6,871,098 B2 | 3/2005 | Wilof-Mindus et al. | |
| 6,907,280 B2 | 6/2005 | Bacerra et al. | |
| 7,010,351 B2 | 3/2006 | Firlik et al. | |
| 7,346,395 B2 | 3/2008 | Lozano et al. | |
| 7,353,065 B2 | 4/2008 | Morrell | |
| 7,653,433 B2 | 1/2010 | Lozano et al. | |
| 7,684,866 B2 | 3/2010 | Fowler et al. | |
| 2002/0013612 A1 | 1/2002 | Whitehurst | |
| 2002/0058867 A1 | 5/2002 | Breiter et al. | |
| 2002/0062143 A1* | 5/2002 | Baudino et al. | 607/116 |
| 2002/0087201 A1 | 7/2002 | Firlik et al. | |
| 2002/0091419 A1 | 7/2002 | Firlik | |
| 2002/0151939 A1 | 10/2002 | Rezai | |
| 2002/0169485 A1 | 11/2002 | Pless et al. | |
| 2003/0028072 A1 | 2/2003 | Fischell et al. | |
| 2003/0097159 A1 | 5/2003 | Schiff et al. | |
| 2003/0149457 A1 | 8/2003 | Tcheng et al. | |
| 2003/0181954 A1 | 9/2003 | Rezai | |
| 2004/0172091 A1 | 9/2004 | Rezai | |
| 2004/0186532 A1 | 9/2004 | Tadlock | |
| 2005/0021118 A1 | 1/2005 | Genau et al. | |
| 2005/0027284 A1 | 2/2005 | Lozano et al. | |
| 2005/0033378 A1 | 2/2005 | Sheffield et al. | |
| 2005/0033379 A1 | 2/2005 | Lozano et al. | |
| 2005/0143799 A1 | 6/2005 | Black et al. | |
| 2005/0143800 A1 | 6/2005 | Lando et al. | |
| 2006/0004422 A1 | 1/2006 | De Ridder | |
| 2006/0015153 A1 | 1/2006 | Gliner et al. | |
| 2006/0106430 A1 | 5/2006 | Fowler et al. | |
| 2006/0212090 A1 | 9/2006 | Lozano et al. | |
| 2006/0212091 A1 | 9/2006 | Lozano et al. | |
| 2006/0259094 A1 | 11/2006 | Naisberg et al. | |
| 2007/0005115 A1* | 1/2007 | Lozano et al. | 607/45 |
| 2007/0203545 A1 | 8/2007 | Stone | |
| 2007/0244519 A1 | 10/2007 | Keacher et al. | |
| 2007/0265489 A1 | 11/2007 | Fowler et al. | |
| 2008/0064947 A1 | 3/2008 | Heruth et al. | |
| 2008/0103548 A1 | 5/2008 | Fowler et al. | |
| 2008/0208285 A1 | 8/2008 | Fowler et al. | |
| 2009/0112281 A1 | 4/2009 | Miyazawa et al. | |
| 2009/0131995 A1 | 5/2009 | Sloan | |
| 2009/0149898 A1 | 6/2009 | Hulvershorn et al. | |
| 2010/0036453 A1 | 2/2010 | Hulvershorn et al. | |

FOREIGN PATENT DOCUMENTS

| | | |
|---|---|---|
| WO | WO 03-043690 | 5/2003 |
| WO | WO 2008017055 A2 * | 2/2008 |

OTHER PUBLICATIONS

Weinberger et al. Pedunculopontine nucleus microelectrode recordings in movement disorder patients. Exp Brain Res; (2008) 188:165-174.*

Giacobbe et al. Deep Brain Stimulation for Treatment-Resistant Depression: A Psychiatric Perspective. Current Psychiatry Reports; (2006) 8:437-444.*

Levy et al. Dual Microelectrode Technique for Deep Brain Stereotactic Surgery in Humans. Neurosurgery; (2007) 60 [ONS Suppl 2]:277-284.*

Mayberg et al. Deep Brain Stimulation for Treatment-Resistant Depression. Neuron; (2005) 45:651-660.*

Ketter et al. Functional Brain Imaging, Limbic Function, and Affective Disorders. The Neuroscientist; (Jan. 1996) vol. 2, No. 1, pp. 55-65.*

Al-Hakim, R. et al., "A Dorsolateral Prefrontal Cortex Semi-Automatic Segmenter," Proceedings of the SPIE Medical Imaging 2006; 6144: 170-177.

Barbas et al. "Topographically Specific Hippocampal Projections Target Functionally Distinct Prefrontal Areas in the Rhesus Monkey, "Hippocampus vol. 5, 1995, pp. 511-533.

Barbas et al., "Projections from the Amygdala to Basoventral and Mediodorsal Prefrontal Regions in the Rhesus Monkey," The Journal of Comparative Neurology, vol. 300, 1990, pp. 549-571.

Barr, Deborah et al., "Induction and Reversal of Long-Term Potentiation by Low- and High-Intensity Theta Pattern Stimulation," The Journal of Neuroscience, 15(7): pp. 5402-5410 (Jul. 1995).

Behrens, T. et al., "Non-invasive mapping of connections between human thalamus and cortex using diffusion imaging," Nature neuroscience, vol. 6 No. 7, pp. 750-757 (Jul. 2003).

Bjorklund et al., "Cell replacement therapies for central nervous system disorders," Commentary, Nature Neuroscience, vol. 3, No. 6, Jun. 2000, pp. 537-544.

Boisgueheneuc, F. et al., "Functions of the Left Superior Frontal Gyrus in Humans: A Lesion Study," Brain, Oxford University Press. Advance Access publication Sep. 1, 2006, pp. 3315-3328.

Bremner, et al., "Reduced volume of orbitofrontal cortex in major depression," Biological Psychiatry, Feb. 2002, 51:4, 273-279.

Bremner, J.D., "Structural Changes in the Brain in Depression and Relationship to Symptom Recurrence," CNS Spectrums, vol. 7, No. 2 Feb. 2002, pp. 129-139.

Budson et al., "Memory Dysfunction," N. Eng. J. Med., 352(7): 692-699, 2005.

Caetano et al., "Anatomical MRI Study of Hippocampus and Amygdalia in Patients with Current and Remitted Major Depression," Psychiatry Research: Neuroimaging vol. 132, 2004, pp. 141-147.

Capel et al, "The influence of electrostimulation on hexobarbital induced loss of righting reflex in rats," Acupunct Electrother. Res. 7(1): 17-26, 1982.

Cohen et al., "Studies of Neuroplasticity With Transcranial Magnetic Stimulation," The Journal of Clinical Neurophysiology, vol. 15, No. 4 (1998).

Cosgrove et al. "Psychosurgery," Neurosurgery Clinicals of North America vol. 6 No. Jan. 1995. pp. 167-176.

Delbello et al., "Magnetic Resonance Imaging Analysis of Amygdala and other Subcortical Brain Regions in Adolescents with Bipolar Disorders," Bipolar Disorders vol. 6, 2004, pp. 43-52.

Diamond et al., "Preclinical Research on Stress, Memory and the Brain in the Development of Pharmacotherapy for Depression," European Neuropsychopharmacology vol. 14, 2004 pp. S491-S495.

Dougherty et al., "Cerebral metabolic correlates as potential predictors of response to anterior cingulotomy for treatment of major depression," J. Neurosurg., 99(6): 1010-7, 2003.

Drevets et al. "Functional Anatomical Correlates of Antidepressants Drug Treatment Assessed Using PET Measures of Regional Glucose Metabolism," European Neuropsychopharmology vol. 12, 2002, pp. 527-544.

Drevets et al. "Subgenal Prefrontal Cortex Abnormalities in Mood Disorders," Nature vol. 386, Apr. 24, 1997, pp. 824-827.

Ebmeier et al. "Cerebral Perfusion Correlates of Depressed Mood," British Journal of Psychiatry vol. 178, 1997, pp. 77-81.

Fossati et al., "Neuroplasticity: from MRI to Depressive Symptoms," European Neuropsychophamacology vol. 14, 2004, pp. S503-S510.

Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).

Galynker et al. "Hypofrontality and Negative Symptoms in Major Depressive Disorder," The Journal of Nuclear Medicine vol. 39, No. 4, Apr. 1998, pp. 608-612.

Goldapple et al., "Modulation of Cortical-Limbic Pathways in Major Depression," Arch Gen Psychiatry, vol. 61, Jan. 2004, pp. 34-41.

Gordon et al., "Parameters for direct cortical electrical stimulation in the human: histopathologic confirmation," Electroencephalography and clinical Neurophysiology, vol. 75, pp. 371-377 (1990).

Haberler et al., "No Tissue Damage by Chronic Deep Brain Stimulation in Parkinson's Disease," Annals of Neurology, vol. 48, No. 3, Sep. 2000, pp. 372-376.

Haldane et al., "New Insights Help Define the Pathophysiology of Bipolar Affective Disorder: Neuroimaging and Neuropathology Findings," Progress in Neuro-Psychopharmacology & Biological Psychiatry, vol. 28, 2004, pp. 943-960.

Herwig, U. et al., "Antidepressant Effects of Augmentative Transcranial Magnetic Stimulation," British Journal of Psychiatry, Nov. 2007. pp. 441-448.

Hilty et al., "A Review of Bipolar Disorder Among Adults," Psychiatric Services vol. 50, 1999, pp. 201-213.

Hodge, Jr., C.J. and Boakye, M., "Biological Plasticity: The Future of Science in Neurosurgery," Neurosurgery, vol. 48, No. 1 (Jan. 2001).

Holmes, A. et al., "Spatiotemporal Dynamics of Error Processing Dysfunctions in Major Depressive Disorder," Arch Gen Psychiatry, vol. 65, No. 2, Feb. 2008, 10 pages.

Huerta et al., "Low-Frequency Stimulation at the Troughts of 0-Oscillation Induces Long-Term Depression of Previously Potentiated CA1 Synapses," Journal of Neurophysiology vol. 75, No. 2, Feb. 1996, pp. 877-884.

Jimenez et al., "A Patient with a Resistant Major Depression Disorder Treated with Deep Brain Stimulation in the Inferior Peduncle," Neurosurgery, 57(3): 585-593, 2005.

Johansen-Berg et al., "Anatomical Connectivity of the Subgenual Cngulate Region Targeted with Deep Brain Stimulation for Treatment-Resistant Depression," Cerebral Cortex, 18:1374-1383, Jun. 2008.

Keightley et al., "An fMRI study investigating cognitive modulation of brain regions associated with emotional processing of visual stimuli," Neuropsychologia, 41(5): 585-96, 2003.

Keightley et al., "Personality influences limbic-cortical interactions during sad mood induciton," Neuroimage, 20(4): 2031-9, 2003.

Kennedy et al., "Changes in regional barin glucose metabolism measured with positron emission tomography after paroxetine treatment of major depression," Am. J. Psychiatry, 158(6): 899-905, 2001.

Ketter, et al., "Functional Brain Imaging, Limbic Function, and Affective Disorders," The Neuroscientist, vol. 2, No. 1, pp. 55-65, (Jan. 1996).

Kido, D. et al., "Computed Tomographic Localization of the Precentral Gyrus," Neuroradiology, May 1980, 5 pages.

Lange et al., "Enlarged Amygdala Volume and Reduced Hippocampal Volume in Young Women with Major Depression," Psychological Medicine vol. 34, 2004, pp. 1059-1064.

Liotti et al., "The role of functional neuroimaging in the neuropsychology of depression," J. Clin. Exp. Neuropsychol., 23(1): 121-36, 2001.

Liotti et al., "Differential Limbic-Cortical Correlates of Sadness and Anxiety in Healthy Subjects: Implications for Affective Disorders," Society of Biological Psychiatry, vol. 48, 2000, pp. 30-42.

Liotti et al., "Unmasking disease-specific cerebral blood flow abnormalities: mood challenge in patients with remitted unipolar depression," Am. J. Psychiatry, 159(11): 1830-40, 2002.

Little et al., "How Common is Resistance to Treatment in Recurrent, Nonpsychotic Geriatric Depression?", American Journal of Psychiatry 155: 8, Aug. 1998, pp. 1035-1038.

Lozano, A. et al., "Subcallosal Cingulate Gyrus Deep Brain Stimulation for Treatment-Resistant Depression," Priority Communication, Notice in the Press, Society of Biological Psychiatry. Copyright 2008, 7 pages.

Mayberg et al., "Cingulate function in depression: a potential predictor of treatment response," Neuroreport, 8(4): 1057-61, 1997.

Mayberg et al., "Clinical correlates of PET- and SPECT-identified defects in dementia," J. Clin Psychiatry, 55 Suppl.: 12-21, 1994.

Mayberg et al., "Deep brain stimulation for treatment-resistant depression," Neuron, 45(5): 651-60, 2005.

Mayberg et al., "Depression in Parkinson's disease: a biochemical and organic viewpoint," Adv. Neurol., 65: 49-60, 1995.

Mayberg et al., "Paralimbic frontal lobe hypometabolism in depression associated with Huntington's disease," Neurology, 42(9): 1791-7, 1992.

Mayberg et al., "Paralimbic hypoperfusion in unipolar depression," J. Nuci. Med., 35(6):929-34, 1994.

Mayberg et al., "Reciprocal Limbic-Cortical Function and Negative Mood: Converging PET Findings in Depression and Normal Sadness," Am. J. Psychiatry 156:5 May 1999, pp. 675-682.

Mayberg et al., "Regional Metabolic Effects of Fluoxetine in Major Depression: Serial Changes and Relationship to Clinical Response," Biological Psychiatry vol. 48, 2000, pp. 830-843.

Mayberg et al., "Selective hypometalbolism in the inferior frontal lobe in depressed patients with Parkinson's disease," Ann Neurol., 28(1): 57-64, 1990.

Mayberg et al., "The Functional Neuroanatomy of the Placebo Effect," American Journal of Psychiatry vol. 159, 2002, pp. 728-737.

Mayberg, "Depression, II: localization of pathophysiology," Am. J. Psychiatry, 159(12): 1979, 2002.

Mayberg, "Frontal lobe dysfunction in secondary depression," J. Neuropsychiatry Clin. Neurosci., 6(4): 428-42, 1994.

Mayberg, "Position emission tomography imaging in depression: a neural systems perspective," Neuroimaging Clin. N. Am., 13(4): 805-15, 2003.

Mayberg, Helen, "Modulating Dysfunctional Limbic-Cortical Circuits in Depression: towards development of brain-based algorithms for diagnosis and optimised treatment," British Medical Bulletin vol. 65, 2003, pp. 193-207.

Mayberg, Helen, "Modulating Limbic-Cortical Circuits in Depression: Targets of Antidepressant Treatments," Seminars in Clinical Neuropsychiatry vol. 7, No. 4, Oct. 2002, pp. 255-268.

Mayberg, Helen; "Limbic Cortical Dysregulation: A Proposed Model of Depression," Journal of Neuropsychiatry vol. 9 No. 3, 1997, pp. 471-481.

Ongur, D. et al., "The Organization of Networks within the Orbital and Medial Prefrontal Cortex of Rats, Monkeys, and Humans," Cerebral Cortex, Mar. 2000, vol. 10., pp. 206-219.

Patterson et al., "Electrostimulation: addiction treatment for the coming millennium," J. Altern. Complement Med., 2(4): 485-91, 1996.

Patterson et al., "Neuro-electric therapy: criticisms of the 1984 Bethlem Study," Br. J. Addict., 84(7): 818, 1989.

Patterson, "Effects of neuro-electric therapy (N.E.T.) in drug addiction: interim report," Bull. Narc. 28(4): 55-62, 1976.

Patterson, "Electrostimulation and opiate withdrawal," Br. J. Psychiatry, 146-213. 1985.

Patterson, "Electrotherapy: addictions and neuroelectric therapy," Nurs. Times, 75(48): 2080-3, 1979.

Petrides, M. et al., "Dorsolateral prefrontal cortex: comparative cytoarchitectonic analysis in the human and the macaque brain and corticocortical connection patterns," European Journal of Neuroscience, vol. 1, pp. 1011-1036, 1999.

Philips et al., "Neurobiology of Emotion Persetion I: The Neural Basis of Normal Emotion Perception," Bio Psychiatry vol. 54, 2003, pp. 515-528.

Philips et al., "Neurobiology of Emotion Persetion II: Implications for Major Psychiatric Disorders," Biol Psychiatry vol. 54, 2003, pp. 515-528.

Quirk, et al., "Stimulation of medial prefrontal cortex decreases the responsiveness of central amygdala output neurons," The Journal of Neuroscience, 2003, 23(25): 8800-8807.

Rajikowska, G. et al., "Cytoarchitectonic Definition of Prefrontal Areas in the Normal Human Cortex: II. Variability in Locations of Area 9 and 46 and Relationship to the Talairach Coordinate System," Cerebral Cortex, Jul./Aug. 1995, pp. 323-337.

Rauch, S. L., "Neuroimaging and Neurocircuitry Models Pertaining to the Neurosurgical Treatment of Psychiatry Disorders," Neurosurg Clin N. Am., vol. 14, 2003, pp. 213-223.

Sander et al., "The Human Amygdala: An Evolved System for Relevance Detection," Reviews in Neuroscience vol. 14, 2003, pp. 303-316.

Semniowicz et al., "Limbic-frontal Circuitry in Major Depression: A Path Modeling Metanalysis," NeuroImage vol. 22, 2004, pp. 409-418.

Sheline, Yvette, "3D MRI Studies of Neuroanatomic Changes in Unipolar Major Depression: The Role of Stress and Medical Comorbidity," Biol Psychiatry, vol. 48, 2000, pp. 791-800.

Shin, et al., "A Functional Magnetic Resonance Imaging Study of Amygdala and Medial Prefrontal Cortex Responses to Overly Presented Fearful Faces in Posttraumatic Stress Disorder," Arch en Psychiatry, vol. 62, Mar. 2005, 273-281.

Soares et al., "The Functional Neuroanatomy of Mood Disorders," J. Psychiat. Res., vol. 31, No. 4, 1997, pp. 393-432.

Starkstein et al., "Depression and cognitive impairment in Parkinson's disease," Brain. 112 (Pt. 5) 1141-53, 1989.

Stefurak et al., "Deep brain stimulation for Parkinson's disease dissociates mood and motor circuits: a functional MRI case study," Mov. Disord., 18(12): 1508-16, 2003.

Temple, "Stem cell plasticity—building the brain of our dreams," Perspectives, Nature Reviews—Neuroscience vol. 2, Jul. 2001, pp. 513-520.

Velasco et al., "Neurobiological Background for Performing Surgical Intervention in the Inferior Thalmic Peduncle for Treatment of Major Depression Disorders," Neurosurgery, 57(3): 439-448, 2005.

Videbech et al., "Hippocampal Volume and Drepression: A Meta-Analysis of MRI Studies," Am. J. Psychiatry vol. 161, No. 11, Nov. 2004, pp. 1957-1966.

Volz, K. et al., "Why am I unsure? Internal and external attributions of uncertainty dissociated by fMRI," NeuroImage 21 (2004), pp. 848-847.

Weissmen et al., "Cross-National Epidemiology of Major Depression and Bipolar Disorder," JAMA vol. 276, No. 4, Jul. 24/31, 1996, pp. 293-299.

Australian Examiner's Report for Application No. 2003295349; Northstar Neuroscience, Inc.; Dec. 2007; 3 pgs; Australian Patent Office.

International Search Report for PCT/US2007/075129 dated Sep. 28, 2008.

International Search Report for PCT/US2008/060739 dated Sep. 8, 2008.

International Search Report for PCT/US2008/085973 dated Dec. 8, 2008.

International Search Report for PCT/US2009/039032 dated Feb. 20, 2010.

* cited by examiner

METHODS FOR TARGETING DEEP BRAIN SITES TO TREAT MOOD AND/OR ANXIETY DISORDERS

CROSS-REFERENCE TO RELATED APPLICATIONS

This application claims the benefit of U.S. Provisional Application No. 61/049,092, filed Apr. 30, 2008, which is incorporated herein by reference.

TECHNICAL FIELD

The present invention relates to a method of treating neurological disorders by identifying an area of the brain such as an area of the subgenual area, and stimulating the identified area thereby treating the disorder.

BACKGROUND

Significant advances in the treatment of depression have been made in the past decade. Since the introduction of selective serotonin reuptake inhibitors (SSRIs), i.e., Prozac®, many patients have been effectively treated with anti-depressant medication. New medications to treat depression are introduced almost every year, and research in this area is ongoing. However, an estimated 10 to 30 percent of depressed patients taking an anti-depressant are partially or totally resistant to the treatment. Those who suffer from treatment-resistant depression have almost no alternatives. Thus, there is a need to develop alternative treatments for these patients.

The use of electrical stimulation for treating neurological disease, including such disorders as movement disorders including Parkinson's disease, essential tremor, dystonia, and chronic pain, has been widely discussed in the literature. It has been recognized that electrical stimulation holds significant advantages over lesioning since lesioning destroys the nervous system tissue. In many instances, the preferred effect is to modulate neuronal activity. Electrical stimulation permits such modulation of the target neural structures and, equally importantly, does not require the destruction of nervous tissue. Such electrical stimulation procedures include electroconvulsive therapy (ECT), repetitive transcranial (rTMS) magnetic stimulation and vagal nerve stimulation (VNS).

Efforts have been made to treat psychiatric disorders with peripheral/cranial nerve stimulation. Recently, partial benefits with vagus nerve stimulation in patients with depression have been described in U.S. Pat. No. 5,299,569. Another example of electrical stimulation to treat depression is described in U.S. Pat. No. 5,470,846, which discloses the use of transcranial pulsed magnetic fields to treat depression. Yet further, U.S. Pat. No. 5,263,480 describes that stimulation of the vagus nerve may control depression and compulsive eating disorders and U.S. Pat. No. 5,540,734 teaches stimulation of the trigeminal or glossopharyngeal nerves for psychiatric illness, such as depression.

Deep brain stimulation (DBS) has been applied to the treatment of central pain syndromes and movement disorders, and it is currently being explored as a therapy for epilepsy. For instance, U.S. Pat. No. 6,016,449 and U.S. Pat. No. 6,176,242 disclose a system for the electrical stimulation of areas in the brain for the treatment of certain neurological diseases such as epilepsy, migraine headaches and Parkinson's disease. U.S. Pat. No. 7,313,442 has shown that stimulation of the inferior thalamic peduncle (ITP) or the reticular thalamic nucleus can treat mood and/or anxiety disorders.

Recently, it has been shown that the subgenual gyrus may be stimulated to provide relief to patients suffering from treatment refractory depression (See US Published Applications; 2005/0033379; 20060212091; 2007/0005115; U.S. Pat. No. 7,346,395). However, it is interesting to note that there is considerable asymmetry in the gyrus amongst patients and also across the right and left hemispheres of a single patient. For example, the gyrus may be flatter or more rounded, or multi-lobed or possible only a single gyrus may exist in some patients. Because of this disparately, it is necessary to determine the appropriate location within the subgenual area to stimulate in order to achieve improvement in at least one symptom of the affective disorder. Thus, the present invention is the first to determine the target area within the subgenual area to stimulate to treat a neurological disorder, for example a mood and/or anxiety disorder.

SUMMARY

In certain aspects of the present invention, the method relates to identifying a region of the brain by presenting to the patient a stimulus to alter neuronal activity in a target area, for example, the subcallosal area; internal capsule, anterior cingulate, nucleus accumbens, caudate nucleus, or a combination thereof; measuring neuronal activity by measuring the activity from at least one electrode; and analyzing the neuronal activity in which an alteration of the neuronal activity in response to the stimuli identifies the brain region within the target area.

Yet further, the present invention can relate to a method of improving at least one symptom in an individual suspected of having a mood and/or anxiety disorder, by measuring neuronal activity by measuring the activity from at least one electrode, wherein the neuronal activity is in response to an emotional stimuli; analyzing the neuronal activity in which an alteration of the neuronal activity identifies a pathological region; and stimulating the identified pathological region, thereby improving at least one symptom in the individual. This method can be performed in a closed loop or an open loop system.

Another embodiment comprises a method of treating depression in a patient, comprising identifying an approximate location of the subgenual area of the patient utilizing neuronal activity evoked by emotional stimuli; implanting a stimulation lead within the patient such that at least one electrode of the lead is near or adjacent to the identified location; generating electrical pulses using an implantable pulse generator (IPG) that is implanted within the patient; conducting the electrical pulses from the IPG through a stimulation lead; and applying the electrical pulses to stimulate neural tissue of the subgenual area of the patient utilizing the at least one electrode of the stimulation lead, wherein the applying the electrical pulses effectively treats the depression of the patient. This method can also be performed in a closed loop or open loop method.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 1A shows a stereotactic atlas image and FIGS. 1B and 1C show the corresponding MRI images.

DETAILED DESCRIPTION

Figure 1A:
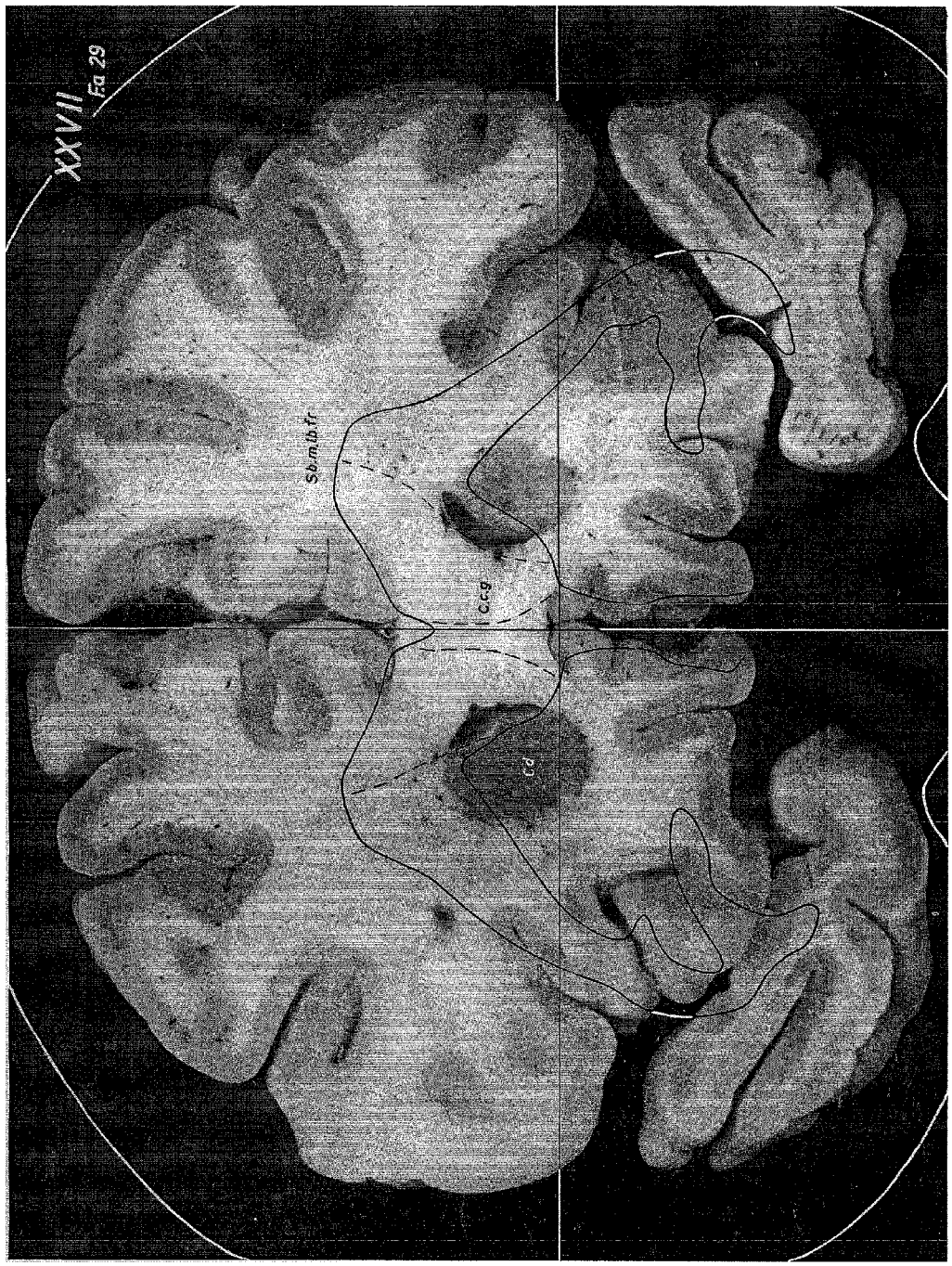
FIGS. 1A-C illustrate targeting of the subgenual area.

It is readily apparent to one skilled in the art that various embodiments and modifications can be made to the representative embodiments in this application without departing from the scope of the appended claims.

I. Identifying Pathological Activity

Some representative embodiments utilize a technique that can identify regions of the brain, for example pathological regions and/or identifying pathological activity that is associated with an Affective disorder or a mood and/or anxiety disorder. Once these regions are identified, then a stimulation program can be implemented to lessen the severity or frequency of the pathological activity and/or terminate the pathological activity or perhaps, prevent the pathological activity.

In certain embodiments, the identification technique utilizes the measurement of neuronal activity or neuronal discharges that occurs as the result of a stimulus, for example emotional stimuli or stimuli that induces traits (e.g., obsessive-disorder traits, stimuli to induce memory or cognitive stimuli). Thus, patients are first selected and/or identified based upon physical, chemical and/or historical behavioral data. Once the patient is selected, then electrodes are inserted into the area of interest, the patient is shown a stimulus to evoke a response and neuronal activity is measured. The neuronal signals are analyzed off line or in real-time, thereby determining a region of the brain that is producing pathological and/or aberrant signals. Thus, these techniques are used to improve targeting areas of the brain or optimize stimulation parameters for neurostimulation to treat neurological disorders or diseases, such as mood and/or anxiety disorders. These techniques can be used preoperatively or intraoperatively as well as in an open loop or closed loop method in combination with stimulation.

In addition to measuring the alterations in neuronal activity or discharge, one of skill in the art is aware that pathological and/or aberrant signals or activities or events can include but are not limited to rate of discharge, pattern of discharge, interspike interval, bursting index, oscillatory behavior, local field potentials (LFPs), electroencephalogram (EEG) changes, magnetoencephalography (MEG) changes, changes in local pH, ionic concentrations (i.e., potassium), concentration of neurotransmitters, changes in temperature, changes in metabolic rate markers, changes in blood flow, and changes in protein and/or gene products. These types of pathological activities or events can be measured using standard techniques available to those of skill in the art.

A. Patient Selection

Subjects to be treated according to some representative embodiments can be selected, identified and/or diagnosed based upon the accumulation of physical, chemical, and historical behavioral data on each patient. One of skill in the art is able to perform the appropriate examinations to accumulate such data. One type of examination can include neurological examinations, which can include mental status evaluations, which can further include a psychiatric assessment. Other types of examinations can include, but are not limited to, motor examination, cranial nerve examination, cognitive assessment and neuropsychological tests (i.e., Minnesota Multiphasic Personality Inventory, Beck Depression Inventory, or Hamilton Rating Scale for Depression). In addition to neurological testing, routine hematological and/or biochemistry testing may also be performed.

In addition to the above examinations, imaging techniques can be used to determine normal and abnormal or pathological brain function that can result in disorders. Thus, once the patient is identified from the above clinical examinations, imaging techniques can be further utilized to provide the region of interest in which the electrodes are to be implanted. Functional brain imaging allows for localization of specific normal and abnormal functioning of the nervous system. This includes electrical methods such as electroencephalography (EEG), magnetoencephalography (MEG), single photon emission computed tomography (SPECT), as well as metabolic and blood flow studies such as functional magnetic resonance imaging (fMRI), and positron emission tomography (PET) which can be utilized to localize brain function and dysfunction.

B. Examination of Activity

Once a patient is identified, then some representative embodiments are utilized to determine a specific location within the brain that exhibits pathological activity. Identification of a brain region that has pathological activity may utilize standard implanted or placed or inserted electrodes to measure and/or record neuronal activity (e.g., the rate of discharge, electrical activity, and/or cellular activity (e.g., neurotransmitter levels, ionic levels, pH levels, etc.)). Neuronal activity that is considered to be pathological in the present invention may comprise an increase in neuronal discharge in response to stimuli (e.g., emotional stimuli, trait inducing stimuli, etc.). Yet further, other neuronal activity that may be considered pathological may comprise changes in response to an external stimulus (e.g., emotional stimuli, trait inducing stimuli, etc.), for example changes in electrical activity measured by an electroencephalogram (EEG), changes in local field potential, changes in a pattern of discharge, interspike interval changes, bursting index changes, changes in oscillatory behavior, magnetoencephalography (MEG) changes, changes in local pH, changes in ionic concentrations (i.e., potassium), changes in concentration of neurotransmitters, changes in temperature, and changes in metabolic rate markers.

While not being bound by the description of a particular procedure, patients who are to have an electrical stimulation lead or electrode implanted into the brain, generally, first have a stereotactic head frame, such as the Leksell, CRW, or Compass, mounted to the patient's skull by fixed screws. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images or functional imaging (PET or SPECTscan, fMRI, MSI), or indirectly using interactive anatomical atlas programs that map the atlas image onto the stereotactic image of the brain.

In certain embodiments, the target site can be a site involved in the limbic-cortical system or one known to be involved in mood and/or anxiety disorders, for example, but not limited to anterior cingulate, internal capsule, anterior limb of the internal capsule, inferior thalamic peduncle, globus pallidus, globus pallidus internus, globus, pallidus externus, subthalamic nucleus (STN), substania nigra, striatum, ventral striatum, putamen, pars reticulate, pars compacta, dorsal cingulate (Brodmann area 24), Brodmann area 25, nucleus accumbens, hypothalamus, amygdala, hippocampus, orbital frontal cortex (Brodmann area 32/10), dorsolateral prefrontal cortex (Brodmann area 9/46), left dorsolateral prefrontal cortex, subcallosal area, subgenal area, subcaudate, caudate nucleus, anterior insula, medial frontal cortex, dorsal anterior cortex, posterior cingulate area (Brodmann area 31), premotor area (Brodmann area 6), parietal region (Brodmann area 40), anterior thalamus, frontal pole, orbital frontal cortex (Brodmann area 11/10), ventro-lateral prefrontal cortex (Brodmann area 47), periaqueductal gray area, and dorsal brainstem.

In preferred embodiments, the site or implant sites include, but are not limited to the subcallosal area comprising the gray and white matter inferior to the corpus callosum and posterior to the anterior most portion of the genu of the corpus callosum, more particularly, the subgenual area, and more particularly, the subgenual gyrus area, and more particularly, subgenual cortex and surrounding white matter, or Brodmann area 25. More specifically, the site associated with the subcallosal area comprises, for example, about 20 to about 40 mm anterior to the anterior commissure. Thus, the electrode may be implanted at a position of about 20 to about 40 mm anterior to the anterior commissure. In addition to this anterior position, the electrode may also be positioned about 0 to about 15 mm from the midline and about 0 to about 10 mm below the intra-commissural line.

Figures 1B, 1C:
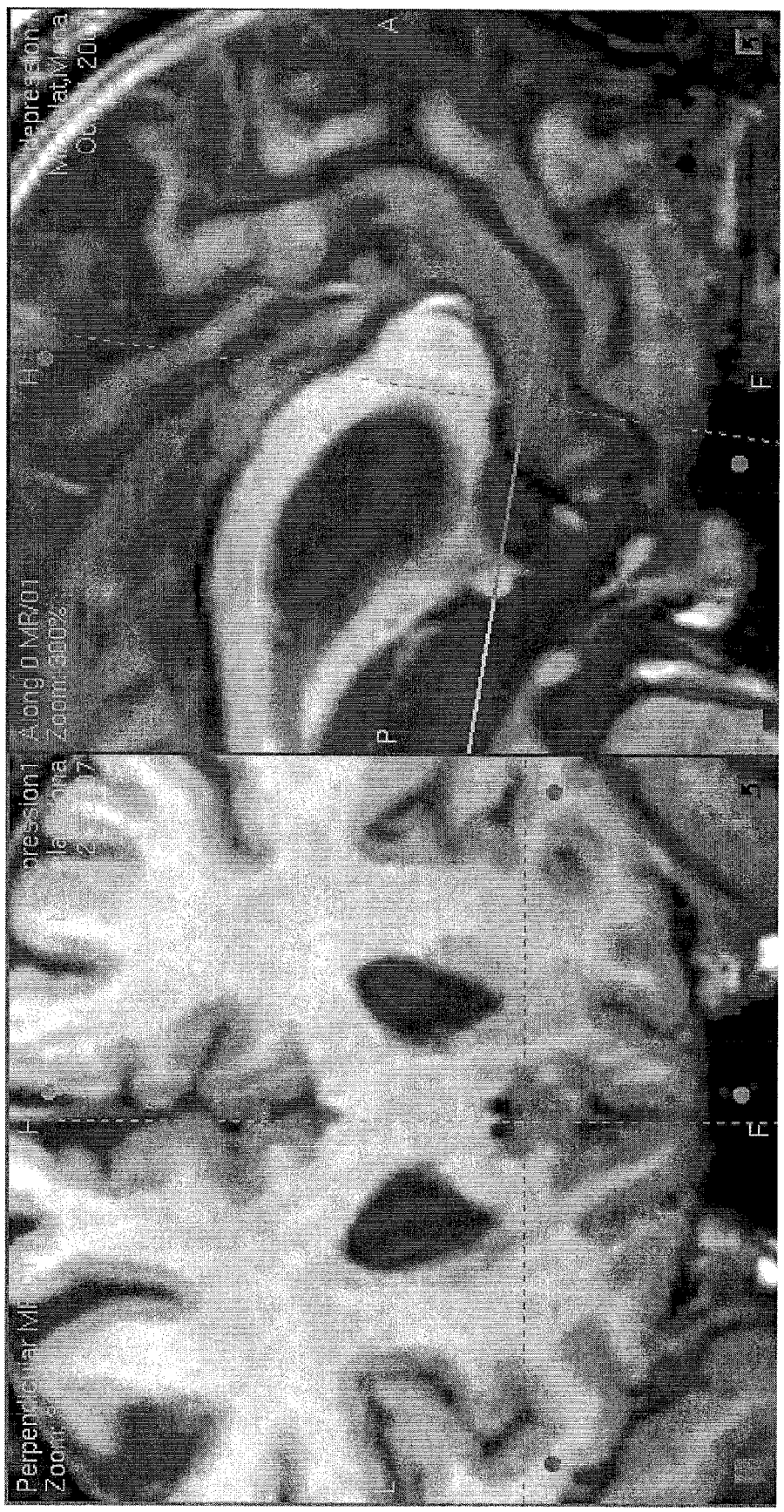

If the implant sites is the subcallosal area, it may be convenient when targeting to utilize a coronal image. Coronal images (T1 or T2 using a 1.5 GE sigma MRI) which are just at or immediately anterior to the anterior most portion of the head of the caudate as shown in FIG. 1A. Typically, this image characteristically goes through the genu of the corpus callosum and enables targeting of the subcallosal area as shown in FIG. 1B.

By selecting appropriate stimulation sites, representative embodiments enable modulation of neuronal activity to affect the neurological disorder. Representative embodiments find particular application in the modulation of neuronal function or processing to affect a functional outcome. The modulation of neuronal function is particularly useful with regard to the prevention, treatment, or amelioration of psychiatric, psychological, conscious state, behavioral, mood, mental activity, cognitive ability, memory and thought activity. Further neurological disorders may include those in which there exists a co-morbidity with depression and/or anxiety, for example, eating disorders including anorexia, bulimia, overeating, etc.

Figure 2:
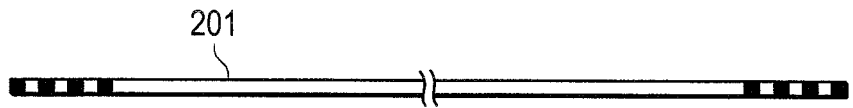
FIG. 2 depicts a stimulation lead that may be employed for implantation within a patient.
Figure 3:
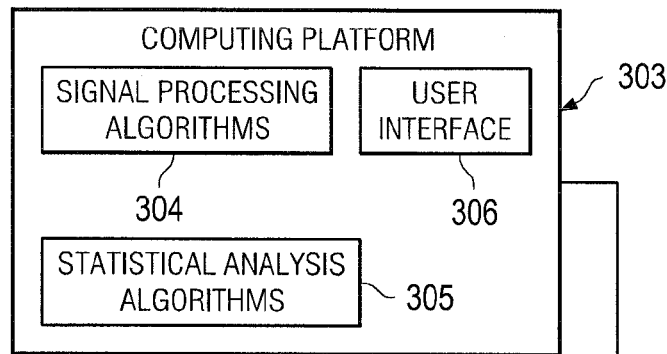
FIG. 3 depicts a system to identify a region within the brain according to one representative embodiment.

Upon implanting a stimulation lead 201, as shown in FIG. 2, with electrodes disposed near, adjacent to, or within the target brain tissue, some representative embodiments utilize the detection and analysis of neuronal activity to confirm that the electrodes are properly positioned. Specifically, terminals of the stimulation lead may be coupled using respective conductors 301 to suitable electronic circuitry 302 to enable measurement of the neuronal activity as shown in FIG. 3. Suitable electronic equipment for initial signal sampling and processing include the Guideline System 3000 available from Axon Instruments and the CED 1401 device available from Cambridge Electronic Designs. Further signal processing may occur on a suitable computer platform 603 using available signal processing and statistical analysis libraries (e.g., MATLAB, peristimulus time histogram). The computer platform may include suitable signal processing algorithms 304 (e.g., time domain segmentation, FFT processing, windowing, logarithmic transforms, etc.). Statistical processing may be applied by statistical analysis algorithms 305. User interface software 306 may be used to present the processed neuronal data, and the results of the analysis using a suitable user interface. If neuronal activity is determined to have altered after processing by algorithms 305, the current position of the electrodes is confirmed as the proper location for subsequent delivery of stimulation pulses to treat the disorder. The location of the electrodes can then be fixed using suitable burr hole cap functionality as an example. If such neuronal activity is not altered, then further adjustment of the electrode position may occur. These targeting procedures or programming can be used in an open loop or closed loop system.

In further representative embodiments, other types of programming may be utilized to improve the identification of the target location. For example, in addition to measurement of neuronal activity (e.g., rate of discharge, pattern of discharge, interspike interval, bursting index, oscillatory behavior, local field potentials (LFPs)) in response to stimuli, a physiological response may also be measured. Such physiological responses include changes that can be recorded using functional imaging, for example, PET, MEG, EEG, fMRI, changes in local pH, ionic concentrations (i.e., potassium), concentration of neurotransmitters, changes in temperature, and changes in metabolic rate markers, etc. Thus, the combination data could improve target identification. Targeting utilizing changes in neuronal activity in response to stimuli provides a means to determine or confirm a therapeutic site intra-operatively in combination with preoperatively targeting using diffusion-weighted magnetic resonance imaging (DWI) or any other preoperatively imaging techniques, such as measuring physiological responses pre-operatively in response to stimuli.

In certain embodiments, the stimulus is emotional. Emotional stimuli can include, but are not limited to disturbing stimuli, sad stimuli, neutral stimuli, happy stimuli, exhilarating stimuli, etc. Those of skill in the art are cognizant that such stimuli can be presented to the patient in a form of images from the International Affective Picture Series set (Lang et al. 1988). Other emotional stimuli can include a mood induction task, for example, a sad recount of autobiographical nature or reading, listening, or writing to induce a mood response. Still further, visual stimuli, such as art work can also be used to induce a mood or emotional response.

In addition to emotional stimuli, stimuli or conditioning training can be used to induce an obsessive-compulsive (OCD) trait, for example, touching something dirty can induce a cleanliness OCD trait. Other stimuli to induce memory or cognition can be used, for example, Wechsler Adult Intelligence Scale-Third Edition (WMS-III), Wechsler Memory Scale-Third Edition (WMS-III), Rey Auditory Verbal Learning Test (RAVLT), California Verbal Learning Test (CVLT), Rey-Osterrieth Complex Figure, or Mini-Mental State Exam (MMSE).

Figure 4:
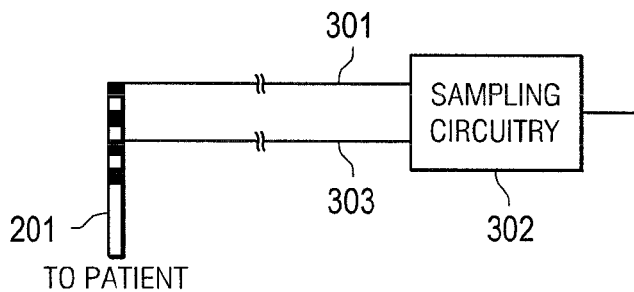
FIG. 4 depicts a stimulation system according to one representative embodiment.
Figure 4:
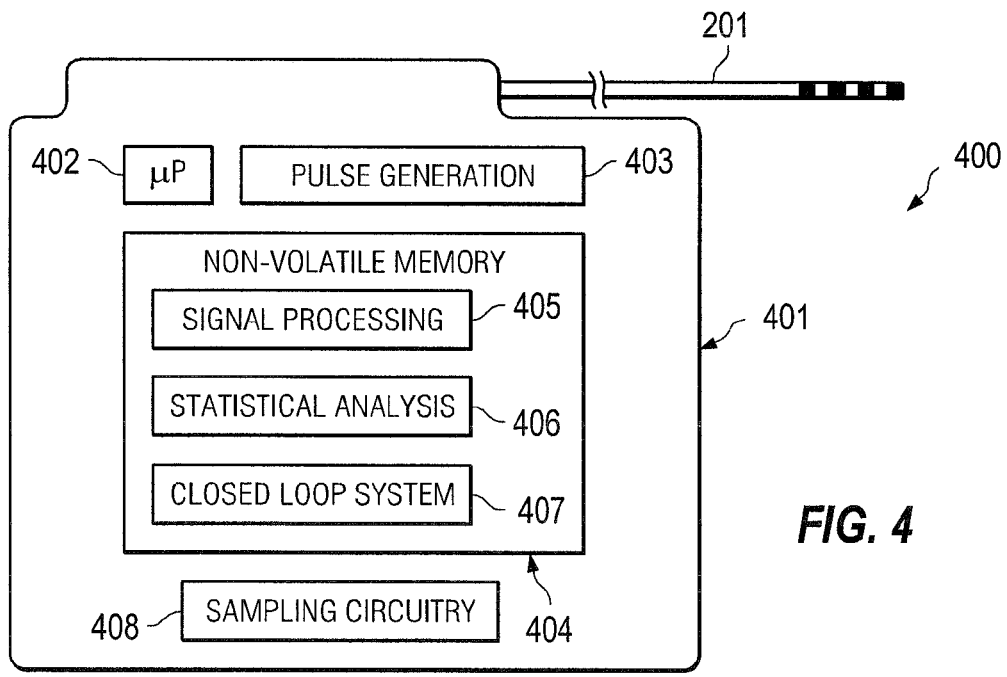

In other representative embodiments, the sampling and processing of the signals representative of the neuronal activity is performed by an implantable pulse generator (IPG). One of skill in the art is aware that commercially available implantable pulse generators can be modified to implement representative embodiments. That is, one of skill in the art would be able to modify an existing IPG to achieve the desired results. An exemplary IPG that is commercially available is the EON® pulse generator (manufactured by Advanced Neuromodulation Systems, Inc.). FIG. 4 depicts IPG 300 adapted according to one representative embodiment. As shown in FIG. 4, IPG 300 comprises processor 402 that possesses sufficient computational capacity to perform the respective digital signal processing and statistical analysis algorithms. The digital signal processing and statistical analysis is preferably performed by software code stored in memory 404 of the IPG (shown as signal processing code 405 and statistical analysis code 406). Closed-loop system code 407 preferably employs the data from code 405 and code 406 to control pulse generation circuitry 403. Additionally, IPG 300 preferably comprises circuitry 408 to facilitate the sampling of the neuronal signals such as an analog-to-digital (AD) converter, amplification circuitry, and/or filtering circuitry. Still further, the sampling circuitry 408 may comprise sampling of other neuronal activities, for example, rate of discharge, pattern of discharge, interspike interval, bursting index, oscillatory behavior, local field potentials (LFPs), physiological responses via functional imaging, such as PET, MEG, EEG, fMRI, and/or other biological responses, such as changes in local pH, changes in ionic concentrations (i.e., potassium), changes in concentration of neurotransmitters, changes in temperature, and changes in metabolic rate markers.

Moreover, sensors that can be used in the present invention can include, for example, epicordical leads, deep brain leads, peripheral leads, drug delivery catheters, combination electrode/catheter leads. Examples of leads that could be used include, a single multi electrode lead with four electrodes each having a width of 2 mm with adjacent electrodes being separated by 2½ mm (as shown as lead 201 in FIG. 2). Another example is a lead with two 1 cm electrodes with a 2 mm intervening gap. Yet further, another example is a 2 or 3 branched lead/catheter to cover the predetermined site or target site. Each one of the prongs may include four electrodes of 1-2 mm width with a center to center separation of 2 of 2.5 mm and a span of 1.5 mm.

II. Treatment of a Neurological Disorder

The present application finds particular application in the modulation of neuronal function or processing to affect a functional outcome. The modulation of neuronal function is particularly useful with regard to the prevention, treatment, or amelioration of psychiatric, psychological, conscious state, behavioral, mood, and thought activity (unless otherwise indicated these will be collectively referred to herein as "psychological activity" or "psychiatric activity" or "mental activity"). When referring to a pathological or undesirable condition associated with the activity, reference may be made to "psychiatric disorder" or "psychological disorder" instead of psychiatric or psychological activity. Although the activity to be modulated usually manifests itself in the form of a disorder such as a mood disorder (i.e., major depressive disorder, bipolar disorder, and dysthymic disorder, refractive depression) or an anxiety disorder (i.e., panic disorder, posttraumatic stress disorder, obsessive-compulsive disorder and phobic disorder), it is to be appreciated that some representative embodiments may also find application in conjunction with enhancing or diminishing any neurological or psychiatric function, not just an abnormality or disorder. Psychiatric activity that may be modulated can include, but not be limited to, normal functions such as alertness, conscious state, drive, fear, anger, anxiety, euphoria, sadness, and the fight or flight response. Furthermore, the methods used herein may also treat psychiatric disorders that are considered to have co-morbidity with mood and/or anxiety disorders. Such disorders may include eating disorders, for example, anorexia, bulimia, binge eating, etc.

In addition to the above, the method described herein can also be used to enhance or improve cognitive abilities in a patient suffering from cognitive impairments and/or memory dysfunction. Such impairments are associated with mild cognitive impairment (MCI), Alzheimer's disease, dementia, post irradiation cognitive impairment, drug-induced depression of cognitive function, cognitive impairment associated with drug use, drug abuse, medication use, epilepsy, hypoxia, anoxia, hypoglycemia, hyperglycemia, post-stoke, post-head injury, metabolic disorders, other psychiatric disorders, movement disorders (e.g., Parkinson's disease, dystonia, chorea, tics and myoclonus). Other forms of cognitive impairment can include those described by Budson and Price in NEJM 2005:352: 692-698, which is incorporated herein by reference can also be treated. Still further, the method can be used to improve motivation, attention, concentration and reward. Thus, stimulation of the predetermined site may be useful to treat attention deficit disorders, drug addiction, disorders of verbal fluency, aphasias, dysphasias, psychomotor retardation, risk-taking behavior, and/or any disorder associated with hypofrontality.

In embodiments where neuronal activity detection and analysis is implemented in an IPG, the stimulation functionality of the IPG is preferably controlled in a closed loop or an open loop manner in response to detection of neuronal activity. In some embodiments, measurements of neuronal activity are made utilizing suitable electrodes of a stimulation lead. For example, the neuronal activity is processed to identify pathological activity in response to a stimulus or sensors are used to detect pathological activity. If neuronal activity is determined to have altered in response to stimuli after processing by algorithms or the sensor has detected pathological activity, the current position of the electrodes is confirmed as the proper location for subsequent delivery of stimulation pulses to treat the neurological disorder. In certain embodiments, another related site that would indirectly alter the pathological neuronal activity may be stimulated. Additionally, the pulse amplitude, pulse width, and pulse frequency may be modified depending upon the detection of the neuronal activity. For example, if stimulation for a predetermined period of time does not reduce or modify the neuronal activity, a control loop (as implemented by software instructions of the IPG) may increase the amplitude or increase the pulse width of the stimulation pulses applied to the target region. When the suppression of the pathological neuronal activity is detected, the electrical stimulation may temporarily cease or the stimulation amplitude or pulse width may be reduced. Thus, these methods can be used to enhance targeting of a site suspected of being therapeutic for the treatment of mood and/or anxiety disorders or optimize parameters to enhance or increase efficiency or efficacy for the treatment of mood and/or anxiety disorders.

The types of stimulation used for the treatment of the pathological findings are known to those of skill in the art. The electrical stimulation can, for example, be long periodic sequences of discrete electrical stimulation pulses or electrical stimulation sequences or patterns. As a consequence of the electrical stimulation used, longer periodic sequences of discrete electrical stimulation pulses typically suppress the pathological activity while electrical stimulation patterns typically bring the activity closer to the natural nonpathologically activity or cause the activity to completely resume the normal nonpathological activity. Any stimulation methodology that is effective in mitigating, reducing, or eliminating the exhibited pathological neuronal activity may be employed by representative embodiments.

Although some representative embodiments have been described in terms of a single integrated device for implantation within a patient, other designs may be employed. For example, an external controller may wirelessly communicate (e.g., using RF communications) with an implantable pulse generator. The wireless communications may communicate the data detected by the sensors of the implanted device and the external controller may process the communicated data. In response to detection of pathological neuronal activity, the external controller may signal the implanted pulse generator to begin stimulating the target neuronal tissue that is exhibiting the pathological activity. Additionally, wireless communication of the neuronal data may be utilized to determine whether the stimulation therapy is effective or whether selected stimulation parameters are no longer optimal.

Using the methods described herein, the predetermined site or target area is stimulated in an effective amount or effective treatment regimen to decrease, reduce, modulate or abrogate the neurological disorder, for example, mood and/or anxiety disorder, more particularly, depression (e.g., treat-resistant major depressive disorder) or obsessive-compulsive disorder. Thus, a subject is administered a therapeutically effective stimulation so that the subject has an improvement in the parameters relating to the neurological disorder including subjective measures such as, for example, neurological examinations and neuropsychological tests (i.e., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS (spell out), CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry. The improvement is any observable or measurable improvement. Thus, one of skill in the art realizes that a treatment may improve the patient condition, but may not be a complete cure of the disease.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

According to one embodiment, the target site is stimulated using stimulation parameters such as, pulse width of about 1 to about 500 microseconds, more preferable, about 1 to about 90 microseconds; frequency of about 1 to about 300 Hz, more preferably, about 100 to about 185 Hz; and voltage of about 0.5 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

It is envisioned that stimulation of an identified or target areas modulates the limbic-cortical circuit or pathway thereby improving any dysfunctional limbic-cortical circuits or cortical-thalamic medial temporal network resulting in an improvement or alleviation or providing remission of depression and/or anxiety or improvement in cognition and/or memory in the treated subjects. Other such improvements can be sensations of calm, tranquility, peacefulness, increased energy and alertness, improved mood, improvement in attention and thinking, improvement in motor speed, improvement in mental speed and in spontaneity of speech, improved sleep, improved appetite (e.g., increase appetite for the subject that is underweight or decrease appetite for the person that is overweight), improved limbic behavior, increased motivation, decreases in anxiety, decreases in repetitive behavior, impulses, obsessions, etc.

For purposes of this application, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether objective or subjective.

Figure 5:
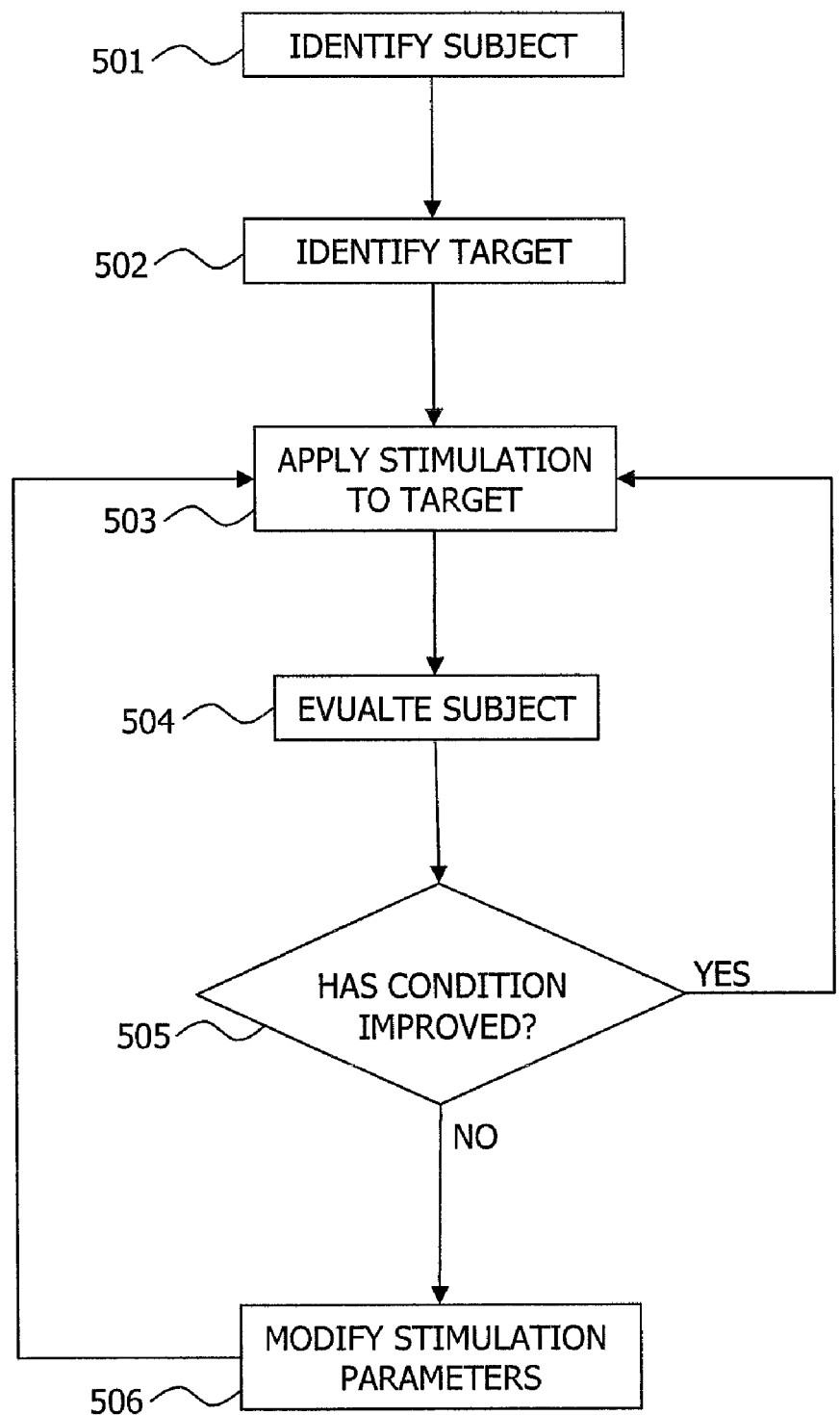
FIG. 5 depicts a flowchart of an exemplary method to treat a neurological disorder.

FIG. 5 summarizes the general procedure according to one representative embodiment. Any of the above described methods can be used to identify a subject or diagnose a subject that suffers from an affective disorder, for example, depression (501). Once the subject is identified, the target site for stimulation is identified using the methods described herein (502). For example, the target site, preferably, may be identified using standard imaging techniques, a combination of imaging techniques and microelectrode recordings and/or microelectrode recordings in the presence of a stimulus to alter neuronal discharges. Once the target site is identified, a stimulation device is implanted into the subject such that the target site, for example, the subcallosal area or subgenual area of the subject's brain is stimulated (503). After the target area has been stimulated (i.e., electrical, chemical, magnetic stimulation or a combination thereof), the subject is evaluated to determine the change in the affective disorder, or for example depression (504). If there is a positive change in the patient's affective disorder, then the stimulation is continuation. If, however, there is no change or there is a negative change in the affective disorder or the stimulation is not optimal, then, the parameters are altered (506), the stimulation is repeated (504) and the subject is evaluated (504). One of skill in the art realizes that the present application is not bound by the described methods or devices and that any method or device that would result in neuromodulation of the target area could be used.

Evaluation of the subject or patient can comprise a variety of techniques well known and used by those of skill in the art. For example, the subject may be evaluated using standard clinical objective or subjective measurements. Subjective measures may include, but are not limited to neurological examinations and neuropsychological tests (i.e., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS (spell out), CGI, N-BAC, or Yale-Brown Obsessive Compulsive score (Y-BOCS)), motor examination, and cranial nerve examination. More objective type measurements may be included in a closed loon or open loop type setting during the evaluating step. For example, a sensor may be included in the stimulation system to sense pathological activity, for example, but not limited to changes in local pH, ionic concentrations, concentration of neurotransmitters, temperature, metabolic rate markers, rate of neuronal discharge, pattern of neuronal discharge, changes in electrical activity, interspike interval, bursting index, oscillatory behavior, or local field potentials. If the sensor is included in a closed loop fashion, then the stimulation is considered responsive therapy or responsive neuromodulation because the system comprises a device to sense alterations in pathological activity and the stimulation can be adjusted based upon the pathological changes. The sensing function may be used in a continuous or non-continuous fashion. One such example of this type of closed loop system comprises a device that is capable of monitoring electrocorticographic signals or local field potential oscillations.

III. Combination Treatment

In further embodiments, it may be desirable to use a drug delivery system independent of or in combination with electrical stimulation of the brain. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, without being bound to a specific procedure, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any suitable type of infusion pump can be used to deliver an appropriate therapeutic agent. For example, active pumping devices or so-called peristaltic pumps, accumulator-type pumps, and/or passive pumping mechanisms can be used to release an agent in a constant flow or intermittently or in a bolus release.

Stimulating drugs comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (i.e., norepinephrine, epinephrine, glutamate, acetylcholine, serotonin, dopamine), agonists thereof, and agents that act to increase levels of an excitatory neurotransmitter(s) (i.e., edrophonium; Mestinon; trazodone; SSRIs (i.e., fluoxetine, paroxetine, sertraline, citalopram and fluvoxamine); tricyclic antidepressants (i.e., imipramine, amitriptyline, doxepin, desipramine, trimipramine and nortriptyline), monoamine oxidase inhibitors (i.e., phenelzine, tranylcypromine, isocarboxasid)), generally have an excitatory effect on neural tissue, while inhibitory neurotransmitters (i.e., dopamine, glycine, and gamma-aminobutyric acid (GABA)), agonists thereof, and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (i.e., bicuculline) and agents that act to decrease levels of an inhibitory neurotransmitter(s) have been demonstrated to excite neural tissue, leading to increased neural activity. Similarly, excitatory neurotransmitter antagonists (i.e., prazosin, and metoprolol) and agents that decrease levels of excitatory neurotransmitters may inhibit neural activity. Yet further, lithium salts and anesthetics (i.e., lidocaine) and/or potassium may also be used in combination with electrical stimulation.

IV. Example

The following example is included to demonstrate preferred embodiments, more particularly methods and procedures, according to some embodiments. It should be appreciated by those of skill in the art that the techniques disclosed in the examples which follow represent techniques discovered by the inventor to function well in the practice of some embodiments of the invention, and thus can be considered to constitute preferred modes of practice. However, those of skill in the art should, in light of the present disclosure, appreciate that many changes can be made in the specific embodiments which are disclosed and still obtain a like or similar result without departing from the spirit and scope of the appended claims.

Example 1

Targeting and Stimulating the Target Site to Treat Depression

Patient Selection

Patients were selected from 3 different clinical sites; Vancouver (UBC), Toronto (UT), and Montreal (MGU). The patients were selected based upon various demographics, for example, family history of depression, age of onset, episodes of depression per year, the past medications and other therapies, and Hamilton Depression rating scores. Table 1 summarizes the criteria used for the patients selected to be treated using electrical stimulation of the subgenual area.

As is known in the art, a score above 7 on the Hamilton Depression Scale (HAMD) is an indication of depression. A 40% change in the HAMD scale score from the initial baseline score is considered a clinical response, while a score of less than 7 is considered clinical remission.

TABLE 1

|  | UBC | MGU | UT | Total |
| --- | --- | --- | --- | --- |
| Number of Patients | 5 | 6 | 7 | 18 |
| Gender | 2 F/3 M | 5 F/1 M | 5 F/2 M | 12 F/6 M |
| Current Age | 43.6 (35-60) | 49.5 (44-53) | 47.9 (39-55) | 47.2 (35-60) |
| Age MDD Onset | 24 (6.2) | 29.7 (10.5) | 26.5 (5.4) | 26.9 (7.6) |
| DSM IV Diagnosis | 5 UP | 6 UP | 7 UP | 18 UP |
| Melancholic Subtype | 4 (80%) | 5 (83%) | 7 (100%) | 16 (89%) |
| # Lifetime Episodes | 4 (4) | 11.5 (8.9) | 5.3 (2.4) | 7.1 (4-25) |
| Current Episode (years) | 5.2 (2-9) | 2.3 (0.5) | 5.4 (3.7) | 4.3 (2-11) |
| Failed Treatments | ≧4 | ≧4 | ≧4 | ≧4 |
| Past ECT | 4 (80%) | 5 (83%) | 7 (100%) | 16 (89%) |
| Past Psychotherapy | 5 (100%) | 6 (100%) | 7 (100%) | 18 (100%) |
| BL Hamilton- D17 Score | 27.4 (4.6) | 28.6 (4.1) | 27.8 (1.8) | 27.9 (3.5) |
| Family History MDD | 4 (80%) | 5 (83%) | 6 (86%) | 15 (83%) |

Preoperative Sterotaxy

Coronal images (T1 or T2 using a 1.5 GE sigma MRI) which were just at or immediately anterior to the anterior most portion of the head of the caudate were chosen from each of the patients (this image characteristically goes through the genu of the corpus callosum), as shown in FIGS. 1B and 1C. Based upon this image, the subgenual cingulate gyrus in the white matter leading into the mesial gray matter of the gyrus was targeted (from approximately 5-7 mm from the most medial border of the gyrus and from 0-15 mm from the midline). The electrodes used had four contacts with a span of 10.5 mm. Thus, the upper most contact was below the inferior surface of the inferior limb of the genu of the corpus callosum and the deepest contact was within the gray matter of the inferior bank of the subgenual cingulate gyrus. The anterior posterior location of the electrode was between 25-40 mm anterior to the anterior commisure.

Figure 6:
FIG. 6 shows the position of all the electrode contacts in the subgenual area.

Patients were operated either under general or local anesthesia. The stereotactic frame was applied under location anesthesia for image acquisition. After the image acquisition the patient was taken to the operating room where under local anesthesia, two burrholes were made 20 mm from the midline and 1 cm anterior to the coronal suture. The dura was coagulated and opened and the pia was coagulated and incised. Once the target sites were identified, two multi contact electrodes were delivered, one in each hemisphere. FIG. 6 illustrates the position of the all the electrodes for all the patients implanted to date.

With the patient's participation, each electrode contact was stimulated and acute changes in behavior was assessed using self report and mood rating scales, such as POMS, PANAS, sadness, anxiety and general well being, self-report, and mood, motor and cognitive scales, such as, finger tapping, verbal fluency. As either positive or negative changes in mood might occur, the relationship between the specific stimulation site and the resulting behavior was carefully documented. Following a testing session to help in optimal target selection and adjustment of the position of the electrode contacts, the incisions were closed and patients taken to the intensive care unit for recovery from surgery.

At anytime after the surgery for implantation of the electrodes, patients underwent a second procedure (~45 mins under general anesthesia) to connect the electrodes to a self contained subcutaneous generator device placed below the clavicle and connected to the electrodes in the head. After 2-3 days, the patients were discharged home on their regular antidepressant regime with the stimulator turned OFF.

In addition to the targeting via imaging, microelectrode recordings can be a useful adjunct. The techniques of the microelectrode recordings are well known and used in targeting the target site for Parkinson's patients and have been previously described. The information that is acquired with microelectrode recording includes the distinction between the bottom of the corpus callosum and the entry into the spare bank of the subgenual gyrus as well as a demarcation of the upper and lower bands of cortex and the intervening white matter. The characteristic firing of neurons in this region is usually slow.

Post Operative Programming:

Patients returned for generator device programming. There were several parameters that were tested, namely, which electrode contact was to be stimulated, the polarity of stimulation, the frequency and pulse width of stimulation, etc.

The electrode programming was done on an outpatient basis and involved a series of trials. The programming of the DBS electrodes can be complex because their response can be delayed and progressive in nature. Typically, an electrode in the white matter was chosen, which was usually, electrode 1 or 2 and it was set at 3.5 volts, 130 Hz and 90 microseconds. These electrode contacts typically produced acute behavioral changes or fMRI signal changes in the subgenual area. This setting was left for two weeks. If at the end of two weeks there was no benefit, then a switch was made to an adjacent pair of electrodes. If there was no response here, then a move was made to the next pair and again to the final $4^{th}$ pair. This would take a total of eight weeks if these changes were made on biweekly methods. If at the end of this eight weeks there was no significant improvement, then the first setting was used and increased the voltage to 5.5 volts and repeated the various settings. If there was no significant response with this then the likelihood of finding further improvements with different electrode combinations was small. If there was improvement at any one of the settings the patient will be left with this setting so that the full course of the improvement can be observed over the course of several weeks. If there is insufficient benefit over time then changing contacts or increasing the current can be considered.

Figure 7:
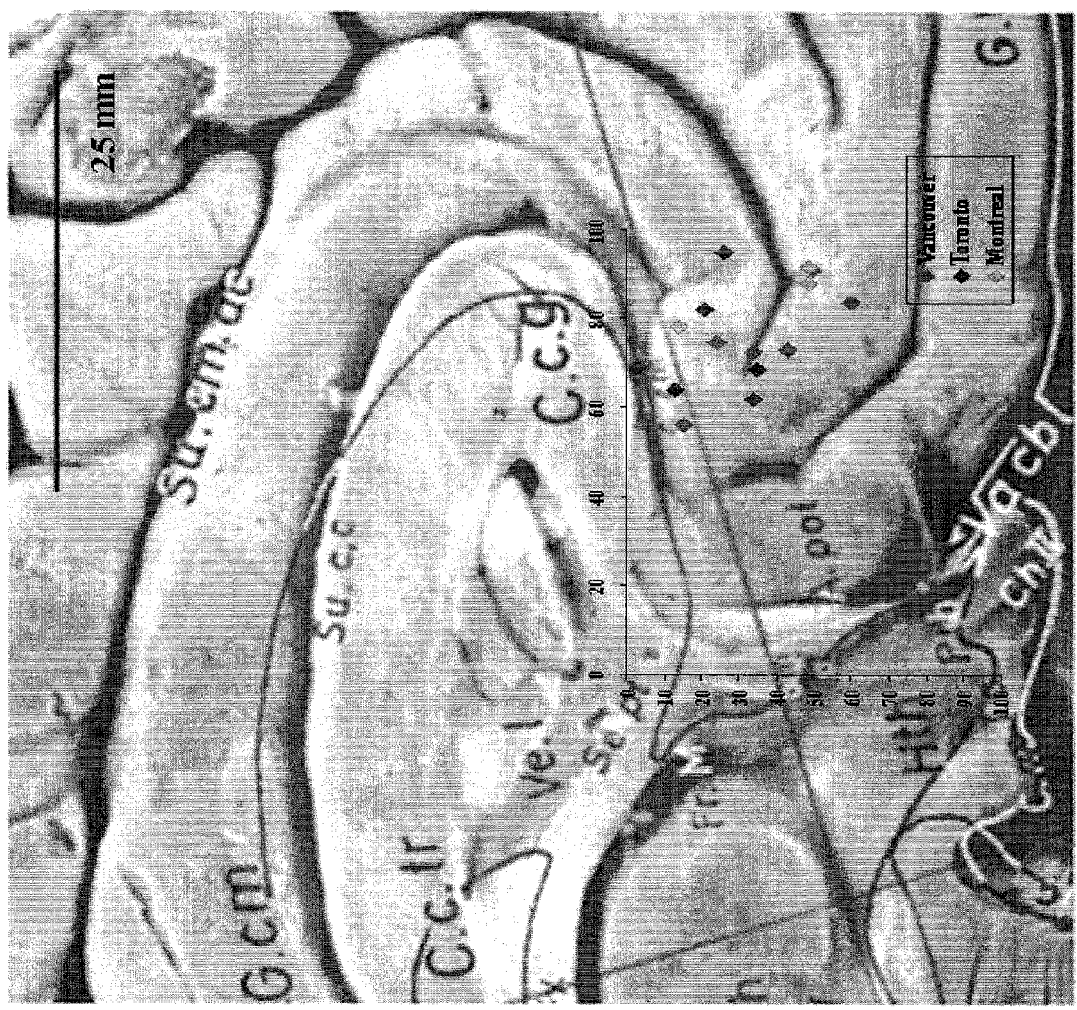
FIG. 7 shows the position of all the electrode contacts of the active responders in the subgenual area.
Figure 8:
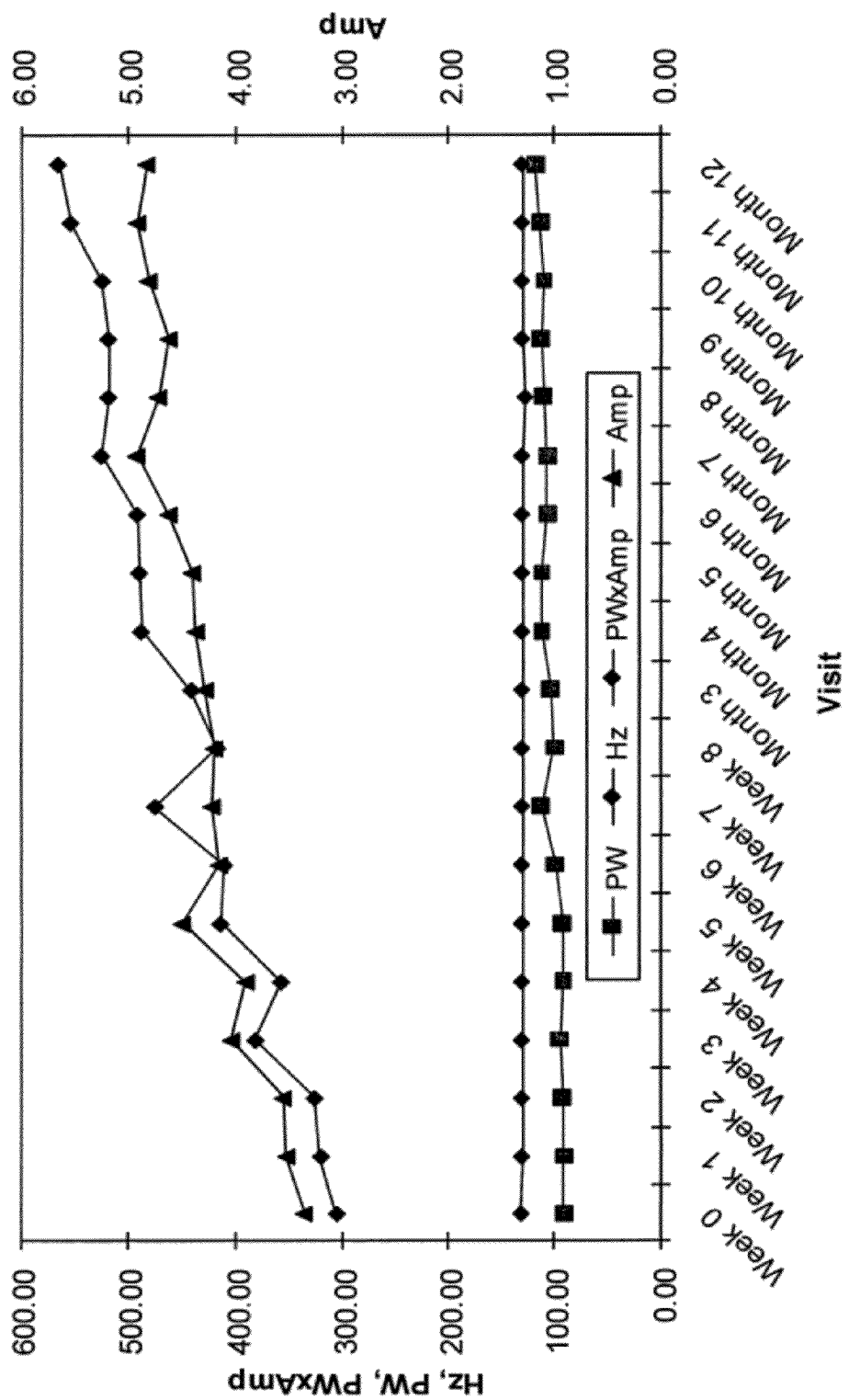
FIG. 8 shows a graph of the average of the programming for the all the patients.

FIG. 7 shows the position of the electrodes from only the positive responders and FIG. 8 shows the average programming from all the patients.

Once final stimulation parameters were established, psychiatric symptoms were monitored on a monthly basis. Clinical ratings were quantified using Beck, Hamilton, CGI, and Quality of Life Scales and Serial Neuropsychological Testing. Serial Neuropsychological Testing and PET studies were performed at 8 weeks and 6 months. General cognitive performance and detailed frontal lobe functioning was assessed. The test battery was designed to differentiate dorsolateral, superior medial, and ventrolateral/orbital frontal behaviors which was differently affected by activation or disruption of the target areas with electrical stimulation. Serial testing allowed differentiation between early surgical effects, chronic stimulation effects, and correlations with mood change.

Figure 9:
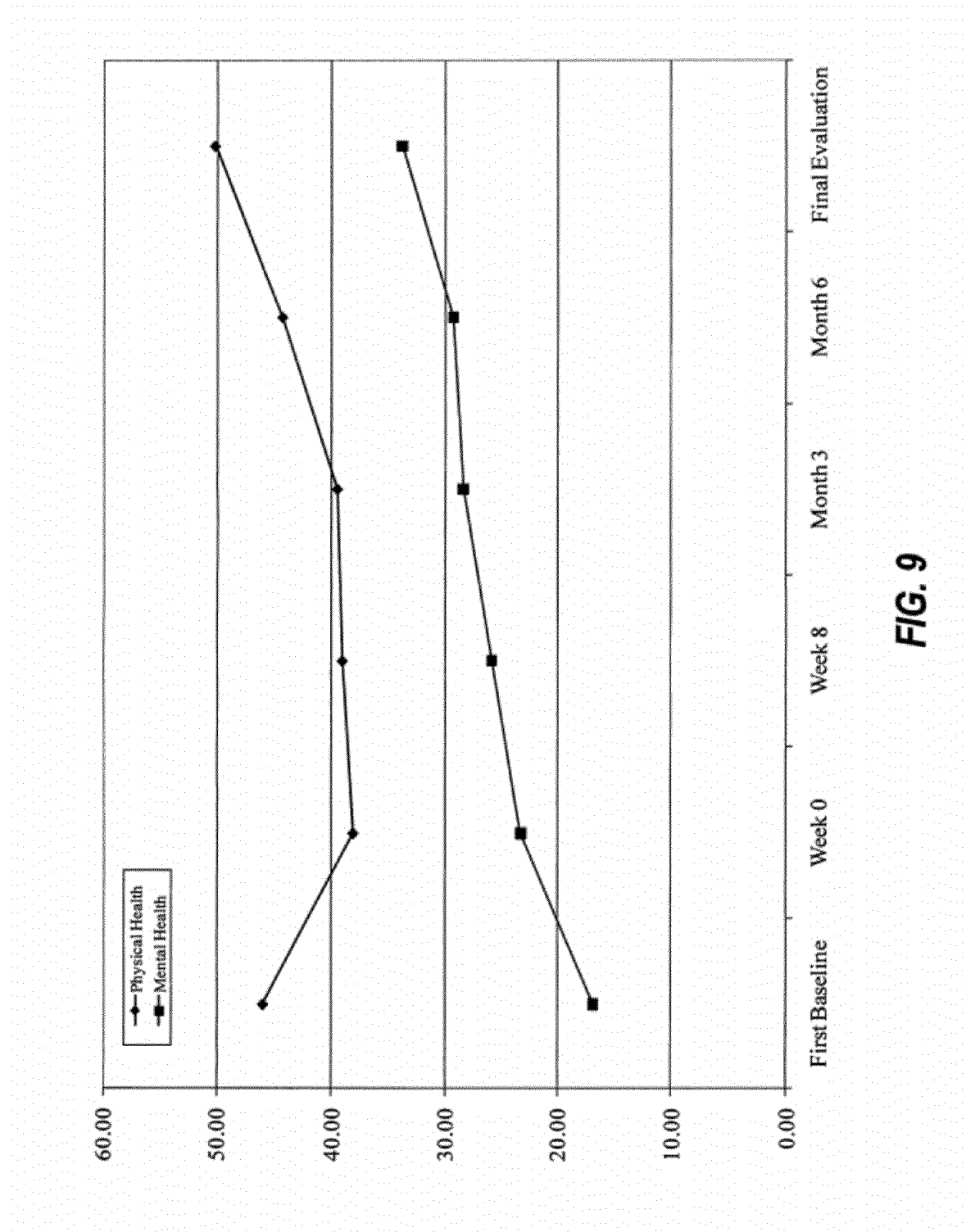
FIG. 9 shows a graph of the average state of mental and physical health for all the patients.
Figure 10:
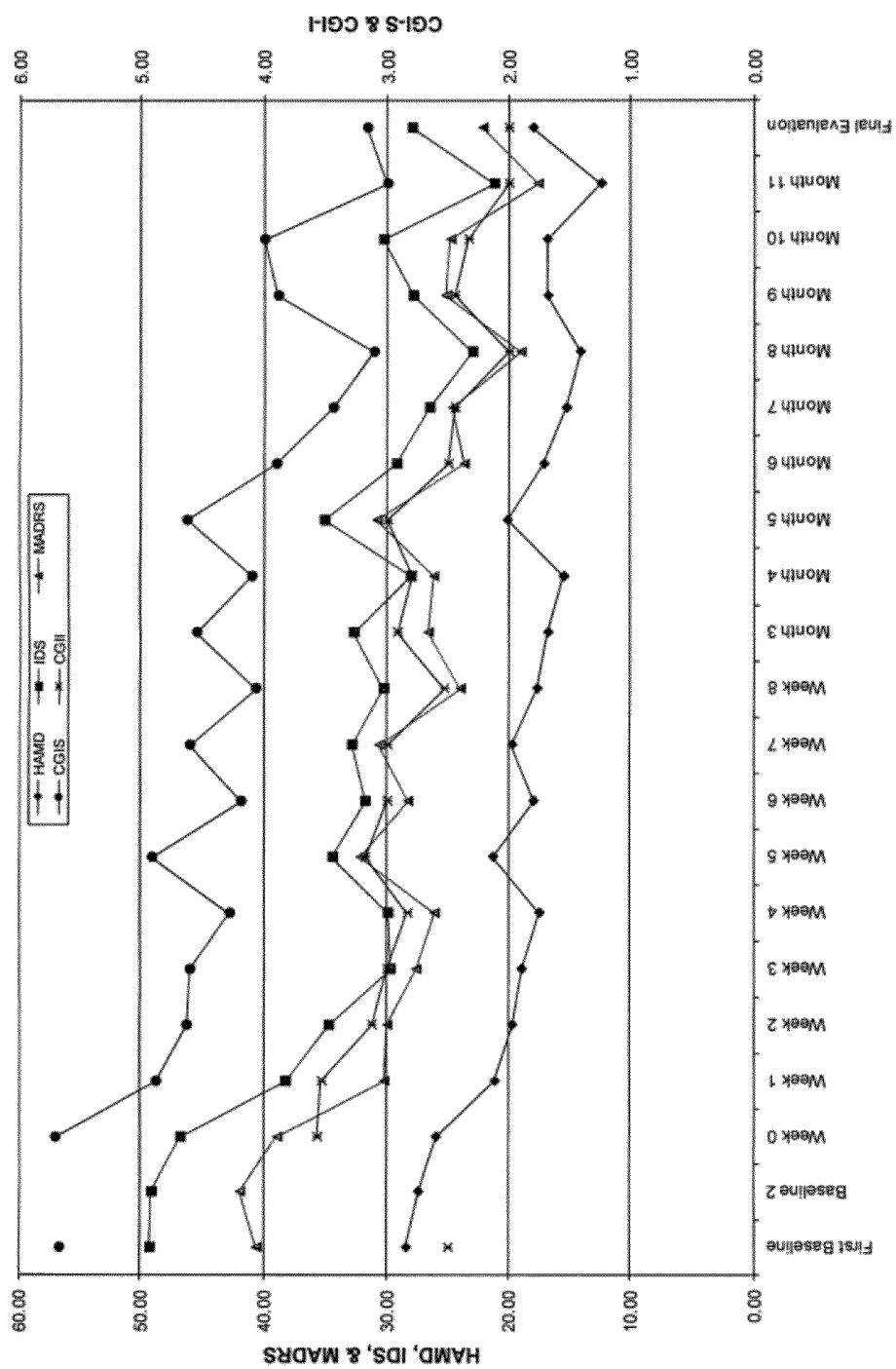
FIG. 10 shows a graph of the total scores from the Hamilton Depression Scale (HAMD), IDS, MADRS, CGIS and CGII in all the patients.

FIG. 9 shows the average mental and physical health of the patients and FIG. 10 and Table 2 show the average change in the scales (HAMD, IDS, MADRS, CGIS, CGII) measured and thus illustrates that stimulation in the subgenual area decreases or attenuates depression.

TABLE 2

Combined Results by Response Status (Mean Scores)

| | Responders (n = 9) | Partial & Non-responders (n = 7) | P value |
|---|---|---|---|
| HRSD-17 Baseline | 27.56 ± 2.9 | 29.14 ± 4.6 | .444 |
| HRSD-17 Month 4/5/6 | 12.44 ± 4.0 | 22.67 ± 4.7 | .001 |
| MASRS-Baseline | 40.33 ± 3.4 | 40.64 ± 5.3 | .895 |
| MADRS-Month 4/5/6 | 20.33 ± 6.6 | 31.62 ± 5.1 | .002 |
| IDS-Baseline | 47.28 ± 6.8 | 46.58 ± 7.7 | .861 |
| IDS-Month 4/5/6 | 23.41 ± 6.9 | 39.38 ± 3.6 | .000 |
| CGI-S Baseline | 5.75 ± 0.9 | 5.71 ± 0.5 | .924 |
| CGI-S Month 4/5/6 | 3.37 ± 1.0 | 5.0 ± 0.8 | .003 |

Example 2

Microelectrode Recordings to Target the Subgenual Area

Participants 7 patients were selected with refractory major depressive disorder (MDD). These patients were undergoing deep brain stimulation subgenual cingulated gyrus, as described above. All seven patients were women in the age range of 38-53.

Microelectrode Recording

Figure 11:
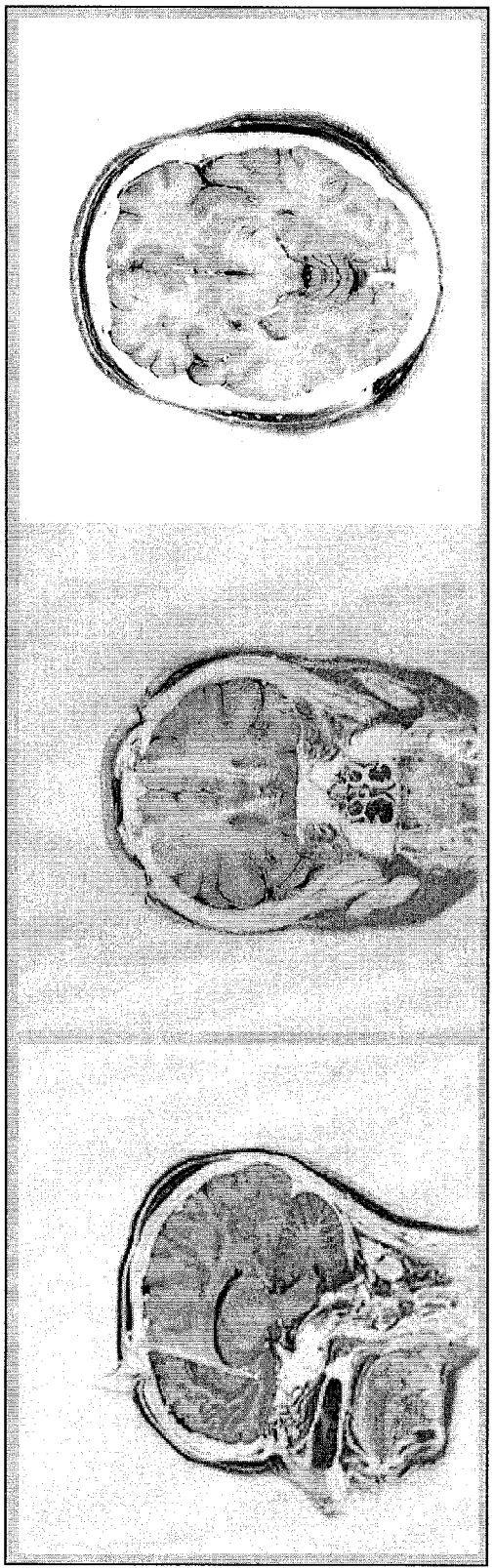
FIG. 11 depicts an exemplary microelectrode recording site.

Microelectrode recordings of single-unit neuronal activity were obtained in each of the 7 patients. 2 Tungsten microelectrodes were used for the recordings. FIGS. 11A-11C illustrates the microelectrode recording sites as the implanted by the above procedure.

Patients viewed sets of emotionally evocative images obtained from the standardized International Affective Picture Series Images from the International Affective Picture Series set (480 photos; Lang et al. 1988). Each image was shown for 2 s followed by a 1 to 3 s fixation screen (a white screen with a black fixation point). The images were separated into categories based on valence (unpleasant to pleasant) and arousal (low to high). The images were presented in random sets of 50 containing 10 images from each of 5 emotion categories based on valence (or pleasantness) and arousal; Type 1: low valence, high arousal, ("disturbing"); Type 2: low valence, high arousal, ("sad"); Type 3: mid valence, low arousal, ("neutral"); Type 4: high valence, low arousal, ("happy"); Type 5: high valence, high arousal, ("exhilarating").

Figure 12:
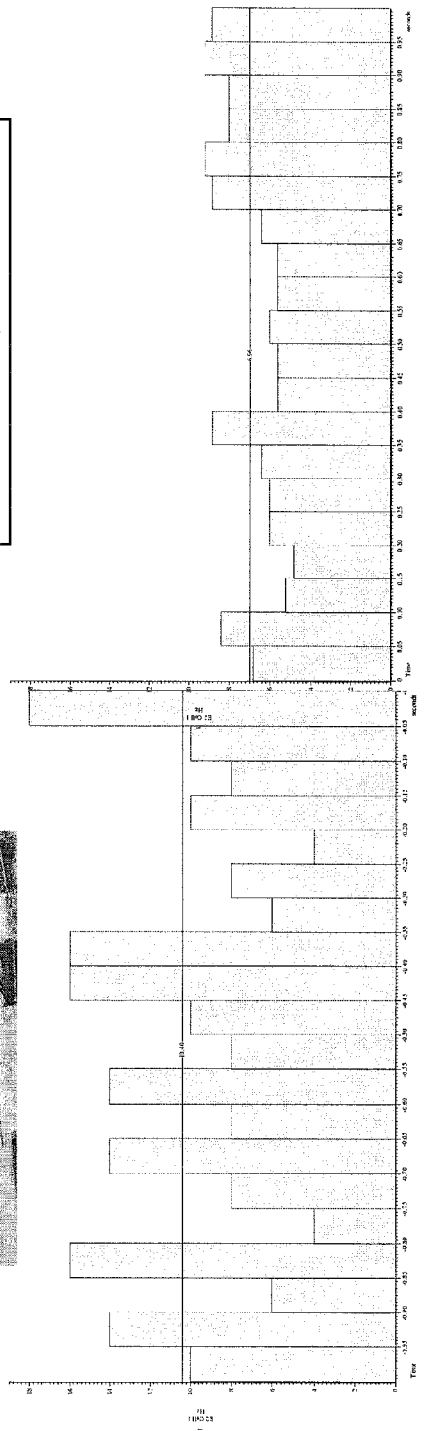
FIG. 12 depicts an image presentation and neuronal response.
Figure 13:
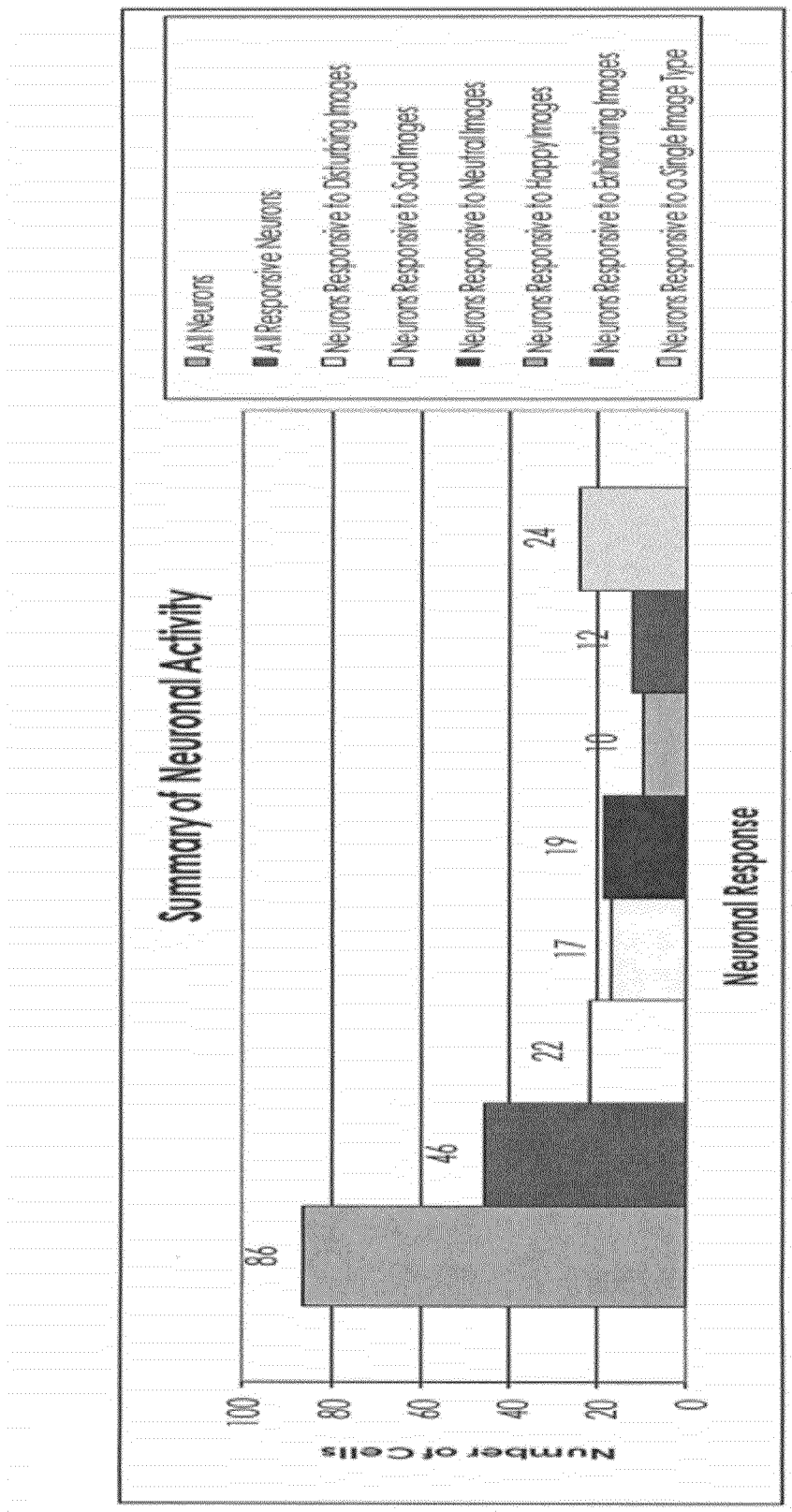
FIG. 13 depicts a graphical representation of the summary of neuronal activity.
Figure 14:
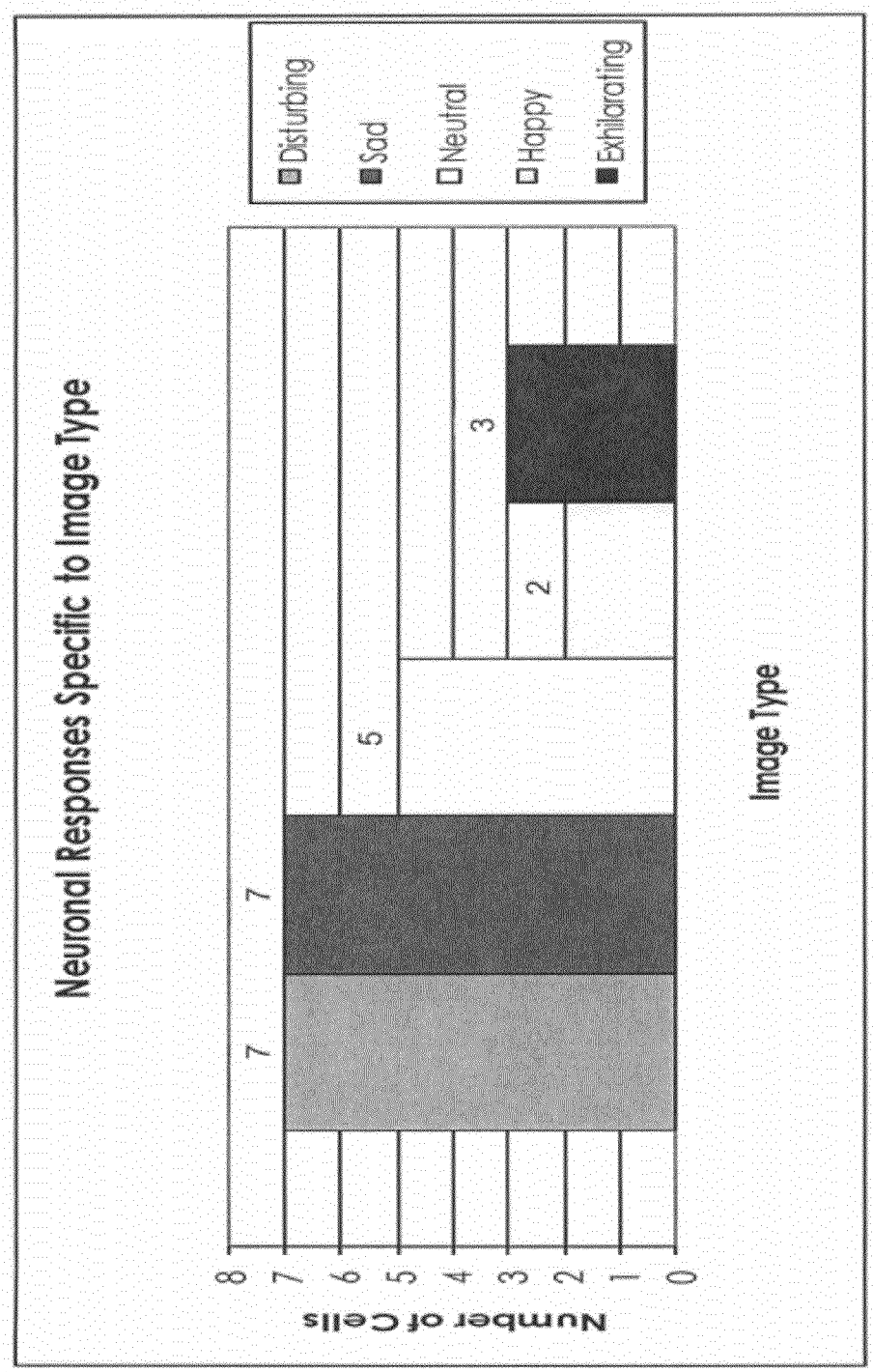
FIG. 14 depicts a graphical representation of neuronal responses to specific image types.
Figure 15:
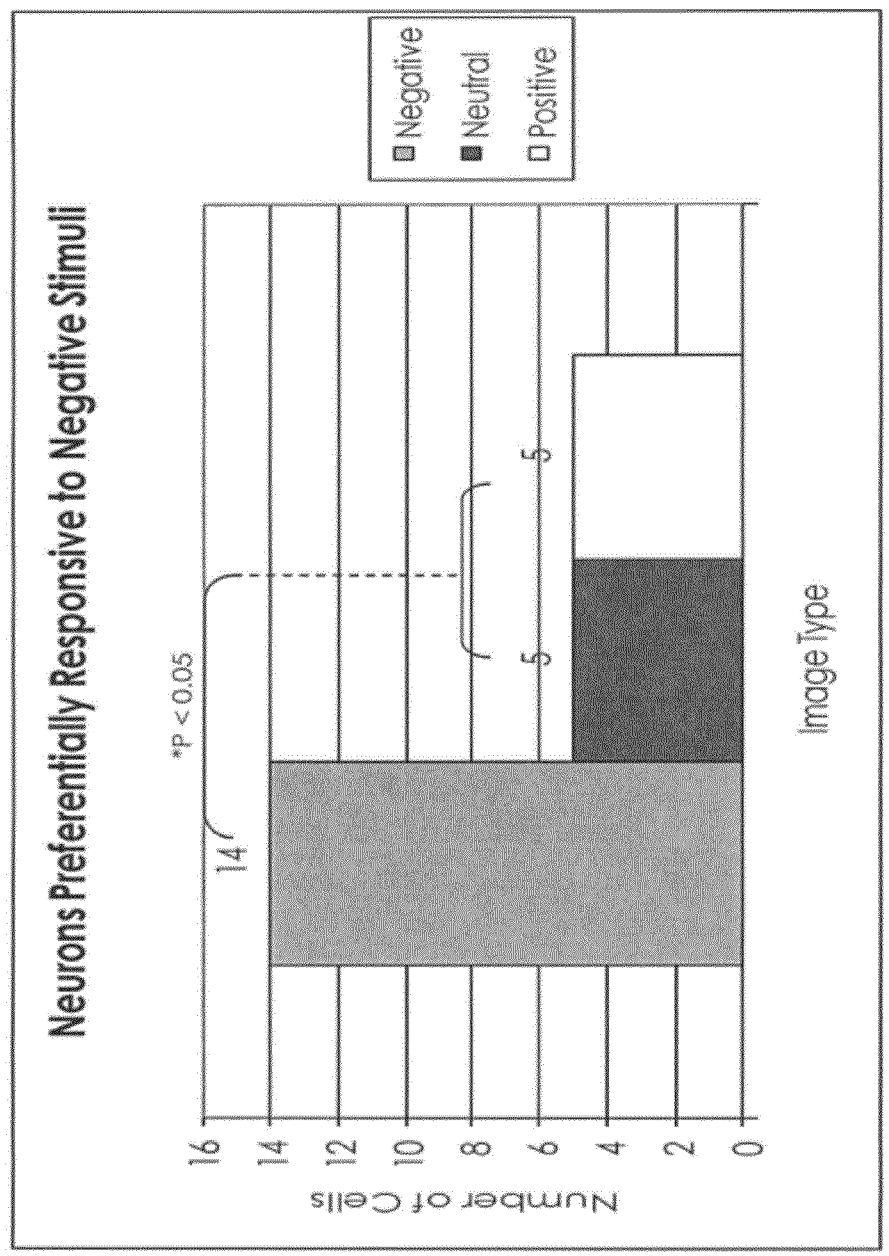
FIG. 15 depicts a graphical representation of neurons preferentially responsive to negative stimuli.
Figure 16:
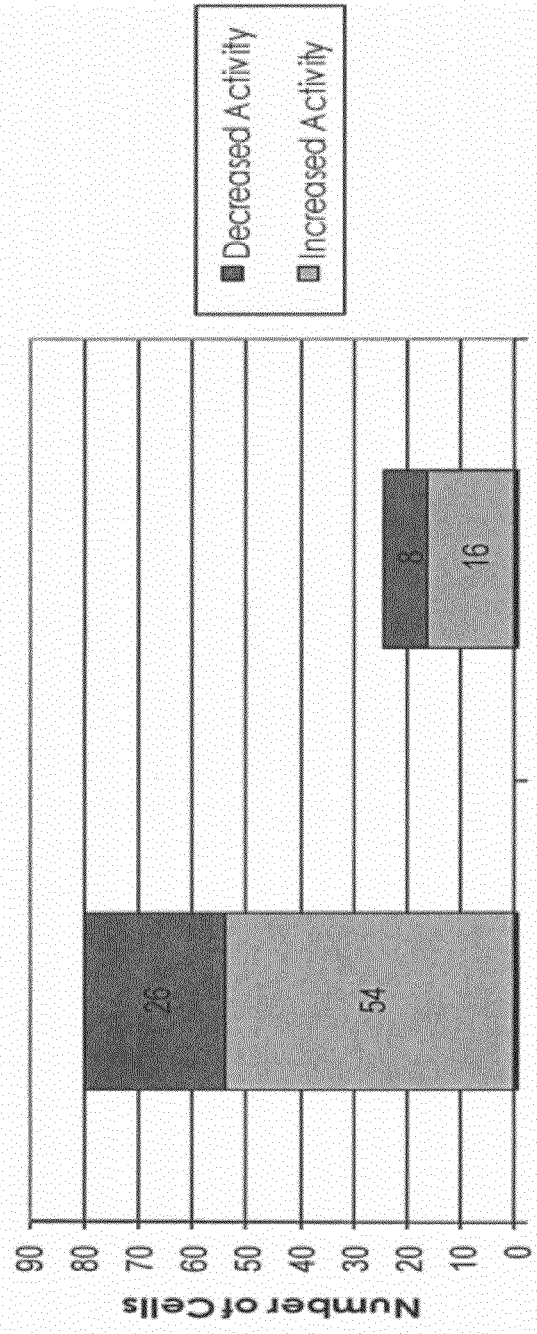
FIG. 16 depicts a graphical representation of responsive neurons preferentially increase activity.
Figure 17:
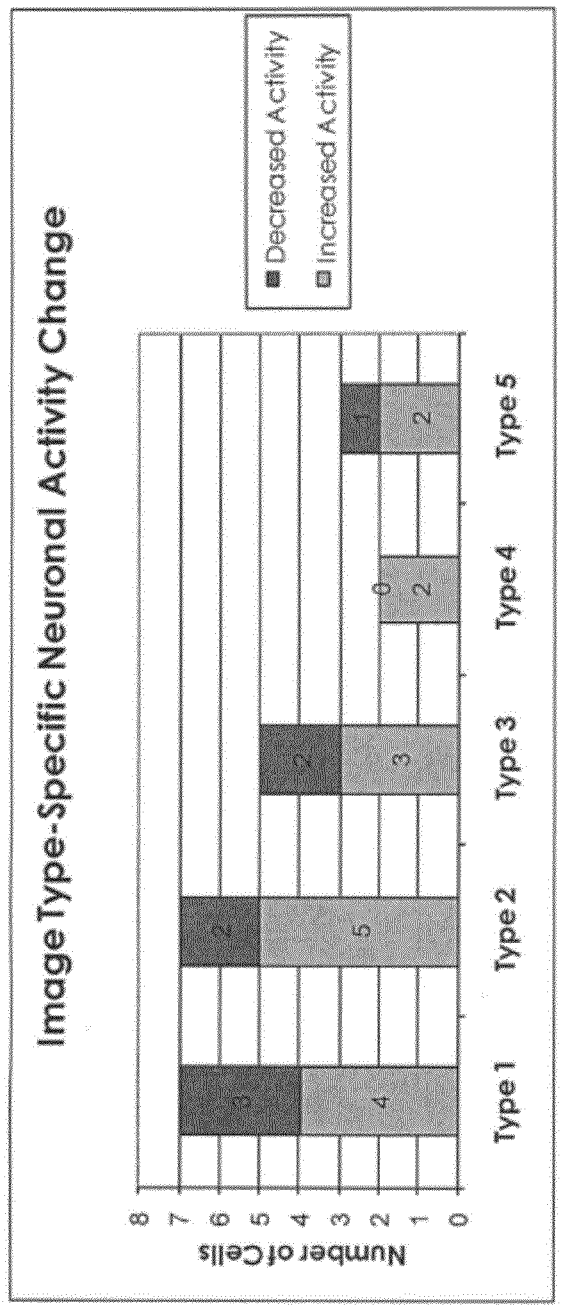
FIG. 17 depicts a graphical representation of image type-specific neuronal activity change.

FIG. 12 provides an illustration of the image and its paired neuronal recordings compared to the fixed point and its paired neuronal recordings.

Results

A total of 86 neurons were recorded. The mean firing rate +/− SD of recorded neurons was 3.25+/−1.92 Hz during the picture viewing task. Forty-six neurons (53.5%) were image responsive (i.e., had a firing rate 2 SD above or below the firing rate during fixation). Twenty-four neurons (27.9%) were responsive to only one image type: 7 (8.1%) to disturbing images, 7 (8.1%) to sad images, 5 (5.8%) to neutral images, 2 (2.3%) to happy images, and 3 (3.5%) to exhilarating images (FIGS. 13-17). Neurons in BA 25 were preferentially responsive to negative images over neutral or positive images (Chi=6.8,p<0.05) (See Table 4. Responsive neurons were more likely to increase rather than decrease activity (Chi=9.8,p<0.01) (See Table 3).

TABLE 3

Responsive Neurons Preferentially Increase Activity

| Comparison | Chi-Square | Probability |
|---|---|---|
| All Responses | 9.8 | 0.002 |
| Image Type-Specific | 2.67 | 0.1 |

TABLE 4

Neurons Preferentially Responsive to Negative Stimuli

| Comparison | Chi-Square | Probability |
|---|---|---|
| −ve vs +/− vs +ve | 6.8 | 0.034 |
| −ve vs +ve | 4.3 | 0.039 |
| −ve vs +/− | 4.3 | 0.039 |
| +ve vs +/− | 0.0 | 1.0 |

Conclusions

Many BA 25 neurons respond to visual stimuli, some showing emotion-responsiveness and emotional valence specific neuronal activity. These results extend previous findings from functional imaging studies demonstrating regional activity changes during emotional processing in BA 25 to the single neuron level among depressed patients. Thus, the use of microelectrode recordings will allow the direct acquisition of cellular activity in this area. It may allow for probing the responses of subgenual cingulate gyrus neurons to emotion stimuli and tasks; therefore resulting in improved targeting methods leading to more efficient stimulation therapy to treat depression and other disorders.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of treating a mood and/or anxiety disorder in a patient, comprising:
    identifying a target area of the subgenual area of the patient by i) positioning an electrode in the subgenual area, ii) presenting to the patient an emotional stimulus to generate pathological neuronal activity, and iii) measuring the neuronal activity, wherein pathological neuronal activity evoked by the emotional stimulus identifies the target area of the subgenual area of the patient; and
    electrically stimulating neural tissue of the identified target area by positioning a stimulation lead in the target area and applying electrical pulses to the target area to treat the mood and/or anxiety disorder of the patient.

2. The method of claim 1, wherein after implantation at least one electrode of the stimulation lead is positioned at about 20 mm to about 40 mm anterior to the anterior commissure.

3. The method of claim 1, wherein after implantation at least one electrode of the stimulation lead is positioned at about 20 mm to about 40 mm anterior to the anterior commissure, about 0 to about 15 mm from the midline and about 3 mm to about 10 mm from the medial border of the gyrus.

4. The method of claim 1, wherein after implantation at least one electrode of the stimulation lead is positioned at about 20 mm to about 40 mm anterior to the anterior commissure, and about 5 mm to about 7 mm from the medial border of the gyrus.

5. The method of claim 1, wherein the mood and/or anxiety disorder is depression.

6. The method of claim 1, wherein the mood and/or anxiety disorder is obsessive-compulsive disorder.

7. The method of claim 1, wherein the subgenual area comprises Brodmann area 25.

8. The method of claim 1, wherein the neuronal activity is measured and analyzed off line or in real-time.

9. A method of improving at least one symptom in an individual suspected of having a mood and/or anxiety disorder, comprising:
    measuring neuronal activity by measuring the activity from at least one electrode that is positioned about 20 to about 40 mm anterior to the anterior commissure, wherein the neuronal activity is in response to an emotional stimuli presented to the patient;
    analyzing the neuronal activity in which an alteration of the neuronal activity identifies a pathological region; and
    providing electrical stimulation to the identified pathological region, thereby improving at least one symptom in the individual.

* * * * *